(12) United States Patent
Williams et al.

(10) Patent No.: US 6,596,513 B2
(45) Date of Patent: Jul. 22, 2003

(54) KLUYVEROMYCES LACTIS MALTASE/MALTOSE PERMEASE BI-DIRECTIONAL PROMOTER AND USE THEREOF

(75) Inventors: Diane P. Williams, Hopkinton, MA (US); William Hintz, Victoria (CA)

(73) Assignee: University of Victoria Innovation and Development Corporation, Victoria (CA)

( * ) Notice: Subject to any disclaimer, the term of this patent is extended or adjusted under 35 U.S.C. 154(b) by 0 days.

(21) Appl. No.: 09/911,909

(22) Filed: Jul. 24, 2001

(65) Prior Publication Data

US 2003/0022281 A1 Jan. 30, 2003

(51) Int. Cl.[7] .......................... C12P 21/02; C12N 1/00; C12N 1/19; C12N 5/10; C12N 15/11; C12N 15/63
(52) U.S. Cl. ................. 435/69.1; 435/243; 435/254.11; 435/254.2; 435/320.1; 435/325; 435/410; 536/24.1
(58) Field of Search ...................... 536/24.1; 435/320.1, 435/325, 243, 410, 69.1, 254.11, 254.2

(56) References Cited

PUBLICATIONS

K.D. Breunig, M. Bolotin–Fukuhara, M.M. Bianchi, D. Bourgarel, C. Falone, I. Ferrero, L. Frontali, P. Goffrini, J.J. Krijger, C. Mazzoni, C. Milkowski, H.Y. Steensma, M. Wesolowski–Louvel and A.M. Zeeman, "Regulation of primary carbon metabolism in Kluyveromyces lactis", Enzyme and Microbial Technology 26 (2000) 771–780..

Carlson, Marian, "Regulation of glucose utilization in yeast", Current Opinion in Genetics & Development 1998, 8:560–564.

Dong, Jinsheng and Dickson, Robert C., "Glucose represses the lactose–galactose regulon in Kluyveromyces lactis through a SNF1 and MIG1–dependent pathway that modulates galactokinase (GAL 1) gene expression", Nucleic Acids Research, 1997, vol. 25, No. 18 3657–3664.

Eckart, Michael R., Bussineau,, Christopher M., "Quality and authenticity of heterologous proteins synthesized in yeast", Current Opinion in Biotechnology 1995, 7:525–530.

Flores, Carmen–Lisset, Rodriguez, Cristina, Petit, Thomas and Gancedo, Carlos, "Carbohydrate and energy–yielding metabolism in non–conventional yeasts", FEMS Microbiology Reviews 24 (2000) 507–529.

Gancedo, Juana M., "Yeast carbon catabolite repression", Microbiology and Molecular Biology Reviews, Jun. 1998, vol. 62, No. 2, p. 334–361.

Gerber, Antonia, Williamson, Peter R., Rex, John H., Sweeney, Erin C., and Bennett, John E., "Cloning and characterization of a candida albicans maltase gene involved in sucrose utilization", Journal of Bacteriology, Nov. 1992, vol. 144, No. 21, p. 6992–6996.

Hong, Seung Hwan and Marmur, Julius, "Primary structure of the maltase gene of the MAL6 locus of Saccharomyces carlsbergensis", Gene, 1986, vol. 41, pp. 75–84.

Hu, Zhen, Yue, Yingzi, Jiang, Hua, Zhang, Bin, Sherwood, Peter W. and Michels, Corinne A., "Analysis of the mechanism by which glucose inhibits maltose induction of MAL gene expression in Saccharomyces", Genetics Society of America, 154 2000, pp. 121–132.

Levine, Joel, Tanouye, Leanne, and Michels Corrinne A., The $UAS_{MAL}$ is a bidirectional promoter element required for the expression of both the MAL61 and MAL62 genes of the Saccharomyces MAL6 locus, Current Genetics, Springer–Verlag 1992, pp. 181–189.

Lundin, Maria, Nehlin, Jan Olof, and Ronne, Hans, "Importance of flanking AT–Rich region in target site recognition by the GC box–binding zinc finger protein MIG1", Molecular and Cellular Biology, Mar. 1994, p. 1979–1985.

Lutfiyya, Linda L., and Johnston, Mark, "Two zinc–finger–containing repressors are responsible for glucose repression of SUC2 expression", Molecular and Cellular Biology, Sep. 1996, p. 4790–4797.

Menne, S., Walz, M., and Kuck, U., "Expression studies with the bidirectional pcbAB–pcbC promoter region from Acremonium chrysogenum using reporter gene fusions", Appl Microbiol Biotechnol (1994) 42:57–66.

Punt, Peter J., Oliver, Richard P., Dingemanse, Maria A., Pouwels, Peter H., and van den Hondel, Cees A.M.J.J., "Transformation of Aspergillus based on the hygromycin B resistance marker from Escherichia coli", Gene, 56 (1978) 117–124.

Schaffrath, Raffael and Breunig, Karin D., "Genetics and molecular physiology of the yeast Kluyveromyces lactis", Fungal Genetics and Biology 30, 173–190 (2000).

Wang, Jianfan and Needleman, Richard, "Removal of a Mig 1p binding site converts a MAL63 constitutive mutant derived by interchromosomal gene conversion to glucose insensitivity", Department of Biochemistry . . . Sep. 28, 1995, p. 51–63.

Wang, Jianfan, Oxana Sirenko and Needleman, Richard, "Genomic footprinting of Mig1p in the MAL62 promoter", The Journal of Biolygcal Chemistry (1997), vol. 272, No. 7, Feb. 14, pp. 4613–4622, 1997.

Zaragoza, Oscar, Rodriguez, Cristina and Gancedo, Carlos, "Isolation of the MIG1 gene from candida albicans and effects of its disruption on catabolite repression", Journal of Bacteriology, Jan. 2000, p. 320–326..

*Primary Examiner*—Terry McKelvey
(74) *Attorney, Agent, or Firm*—Klarquist Sparkman, LLP

(57) ABSTRACT

The present invention concerns DNA sequences from the *K. lactis* maltase/maltose permease genes having transcriptional activity, expression vectors comprising these sequences and their use for the production of proteins.

16 Claims, 9 Drawing Sheets

Figure 3:
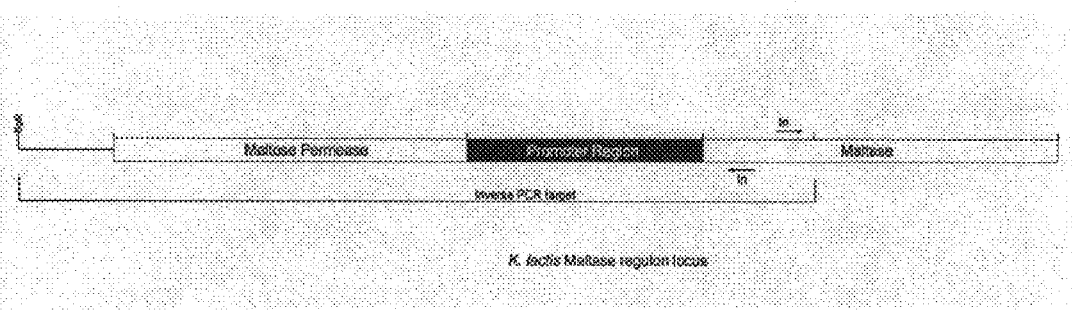

FIG. 1: Secretion of protein from cultures of *Kluyveromyces lactis*.
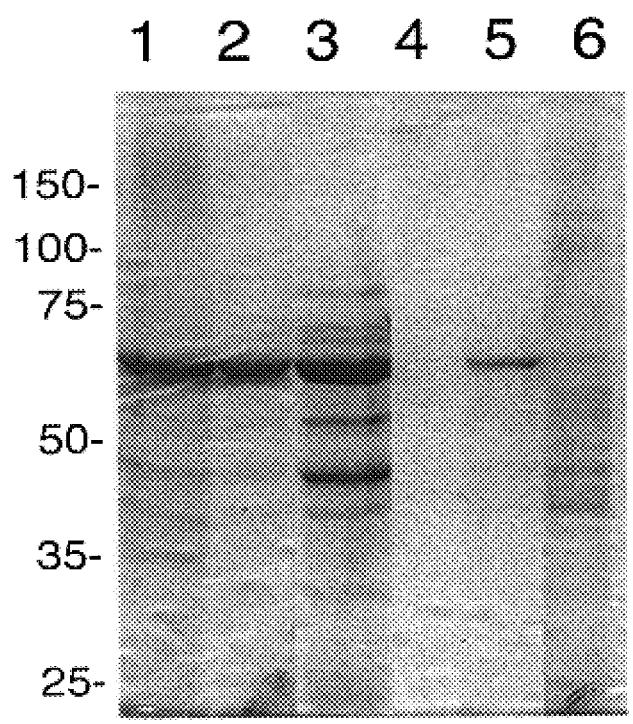

FIG. 2: Multiple sequence alignment of the maltase polypeptide sequences

```
1 -TITKESEPQTDDKWWKEA----------------------------------------- 60
2 MTISDH--PETEPKWWKEATIYQIYPASFKDSNNDGWGDLKGITSKLQYIKDLGVDAIWV60
3 MTISSAH-PETEPKWWKEATIYQIYPASFKDSNNDGWGDMKGIASKLEYIKELGADAIWI60
4 M--------SEHKWWKEAVVYQIWPASYKDSNGDGVGDIPGIISTLDYIASLGVTTVWL60

1 -----------------------------------------------------------120
2 CPFYDSPQQDMGYDISNYEKVWPTYGTNEDCFELIDKTHKLGMKFITDLVINHCSTEHEW120
3 SPFYDSPQDDMGYDIANYEKVWPTYGTNEDCFALIEKTHKLGMKFITDLVINHCSSEHEW120
4 SPMYDSPQDDMGYDVSDYENVYSKYGTLQDMDRLIAGCHDRGLKLILDLVINHTSVEHKW120

1 -----------------------------------------------------------180
2 FKESRSSKTNPKRDWFFWRPPKGYDAEGKPIPPNNWKSFFGGSAWTFDETTNEFYLRLFA180
3 FKESRSSKTNPKRDWFFWRPPKGYDAEGKPIPPNNWRSYFGGSAWTFDEKTQEFYLRLFC180
4 FKESRLSKDNPKRDWYIWKPPRI-DSNGNKHPPNNWGSYFSGSAWKYDELTGEYYLHLFA180

1 --QPDLNWENEDL-NAIYESAVGFWLDHGVDGFRI-------------------------240
2 SRQVDLNWENEDCRRAIFESAVGFWLDHGVDGFRIDTAGLYSKRPGLPDSPIFDKTSKLQ240
3 STQPDLNWENEDCRKAIYESAVGYWLDHGVDGFRIDVGSLYSKVAGLPDAPVIDENSKWQ240
4 ESQPDLNWENKECREAIYNSAIKFWLDKGVDGFRIDTAGMYSKYQHFKDAPVAFPDTEFQ240

1 -----------------------------------------------------------300
2 HPNWGSHNGPRIHEYHQELHRFMKNRVKDGREIMRVGEVAHGSDNA--LYTSAARYEVSE300
3 PSDPFTMNGPRIHEFHQEMNKFIRNRVKDGREIMTVGEMQHATDETKRLYTSASRHELSE300
4 -CEIYHKNGPRIHEFHKEMAKVM-----EPYDTMTVGEVGHSTREQALKYVSAAEKEMNM300

1 -----------------------------------------------------------360
2 VFSFTHVEVGTSPFFRYNIVPFTLKQWKEAIASNFLFINGTDSWATTYIENHDQARSITR360
3 LFNFSHTDVGTSPKFRQNLIPYELKDWKVALAELFRYVNGTDCWSTIYLENHDQPRSITR360
4 MFLFDVVELGSDPRDRFRYNGFDLVDLKKAIKSQGEFAEGTDAWSTVFIENHDQARAISR360

1 -----------------------------------------------------------420
2 FADDSPKYRKISGKLLTLLECSLTGTLYVYQGQEIGQINF-KEWPIEKYEDVDVKNNYEI420
3 FGDDSPKNRVISGKLLSVLLVSLSGTLYVYQGQELGEINF-KNWPIEKYEDVEVRNNYDA420
4 FGNDSPEFRVLSGKAIAMLQCCLTGTLFIYQGQEIGMTNVPRSWPIEEYKDINTINYYRA420

1 -----------------------------------------------------------480
2 IKKSFGKNSKEMK---DFFKGIALLSRDHSRTPMPWTKDKPNAGFTGPDVKPWFFLNESF480
3 IKEEHGENSKEMK---RFLEAIALISRDHARTPMQWSREEPNAGFSGPNAKPWFYLNESF480
4 FKEKYGKDADYKQKEEKLVDVINRLARDNARTPVQWSHQQYAGFSEVEPWMRVNDNYKE-480

1 -----------------------------------------------------------540
2 EQGINVEQESRDDDSVLNFWKRALQARKKYKELMIYGYDFQFIDLDSDQIFSFTKEYEDK540
3 REGINAEDESKDPNSVLNFWKEALRFRKAHKDITVYGYDFEFIDLDNKKLFSFTKKYDNK540
4 ---INVEDQDGDDHSLLNFYRKLLKLRGEYKDLFVYG-EMKFLDFDDKKLFTFAKEAPGS540

1 -----------------------------------------------------------595
3 TL-FAALNFSGEEIEFSLPREGASLSFILGNYDDTDVSSRVLKPWEGRIYLVK--595
3 TL-FAALNFSSDSIDFTIPNNSSSFKLEFGNYPRSEVDASSRTLKPWEGRIYISE595
4 PVAYIVINFSGEDVKFEPLIKGNYKLVLTNVDKDSKDALSPYEARMYVV------595
```

FIG. 4A: Sequence comparison of the maltase/maltose permease promoter region from *K. lactis* CBS1065 and 2359/152 (Accession No. AJ007636).

```
CBS 1065   TTGCCACGCTAGAACTATGTTGTCGATCAACCCACGCCAGTTAATGTCATATTTATAAGA
2359/152   TTGCCACGCTAGAACTATGTTGTCGATCAACCCACGCCAGTTAATGTCATATTTATAAGA

CBS 1065   ATTATCACAGCTTTCCTCATACTGGATATTGTCATGAAGCTCAAGAACATTGTTTGTACT
2359/152   ATTATCACAGCTTTCCTCATACTGGATATTGTCATGAAGCTCAAGAACATTGTTTGTACT

CBS 1065   GACATCTAGAATAATGAGGTGAAGTGATTAAATCGGGGACCAGAACACAGAAAAACCCTG
2359/152   GACATCTAGAATAATGAGGTGAAGTGATTAAATCGGGGACCAGAACACAGAAAAACCCTG

CBS 1065   CACAGCCGTTTTTACTTTTTTCGCACTAGTTGCCGAAGAAACTGACCGAGAATTGTACTC
2359/152   CACAGCCGTTTTTATTTTTT-CGCAGTAGTTGCCGAAGGAACTGACCGAGAA--AAAATC
                                                        ← Lac9p →
CBS 1065   CATTGAAATCCG--CATGGAT-ACTTG-ACTAAATGGTGGGGT-ACC-AGTTTTGCTTCT
2359/152   CATTTAAATCCGGCCTTGGATAACTTGGACTAAATGGTGGGGTTACCCAGTTTTGCTTCT
                                     Mig1 →
CBS 1065   CTCTCC-GATTCAACATTTCATACCGTTTTACCGCCT-GAAATGGCACTTGCAATGAATC
2359/152   CTCTCCCGATTCAACATTTCATACCGTTTTACCGCCTTGAAATGGCACTTGCAATGAATC

CBS 1065   TTTT-GTGAACATTCTTTGTTACCCCGG-ATTTTCTTCCG-ATGTATGAAAACAAATATG
2359/152   TTTTTGTGAACATTCTTTGTTACCCCGGGATTTTCTTCCGGATGTATGAAAACAAATATG
                              ← Mig 1/Lac9p              IR   Mig1 →
CBS 1065   GGGAAAAACATGGTGAAGACGGAAAATCTCTGCATACTTTTTGTGTTTGGGAAACCAAAG
2359/152   GGGAAAAACATGGTGAAGACGGAAAATCTCTGCATACTTTTTGTGTTTGGGAAACCAAAG

CBS 1065   CGACATTTGAGATAAGGCTGTTCTATAGAATTCACGTACAGGAAAATTTCCACCCGTATT
2359/152   CGACATTTGAGATAAGGCTGTTCTATAGAATTCACGTACAGGAAAATTTCCACCCGTATT
                                 palindrome              UAS ←
CBS 1065   ACTTGTGACCACATCTGGGGAGATTTCATTTTTTTGCCCTTTTCACTTTCCTCACAGAA
2359/152   ACTTGTGACCACATCTGGGGAGATTTCATTTTTTTGCCCTTTTCACTTTCCTCACAGAA CBS 1065   ACTACGTTTTTCCTTTTCCCTCGAGAAAATTTCTCCATTTTTCCGTTTCCCTCGAGCAAA
2359/152   ACTACGTTTTTCCTTTTCCCTCGAGAAAATTTCTCCATTTTTCCGTTTCCCTCGAGCAAA
                                  UAS ←
CBS 1065   GTTTCTATTACTTTTAGTTGAAACTACTAACTTTTGTTTTTCAAAAAAAATTGGCTGCAT
2359/152   GTTTCTATTACTTTTAGTTGAAACTACTAACTTTTGTTTTTCAAAAAAAATTGGCTGCAT
                                   Inverted repeat (IR)
CBS 1065   TCAACAGAATGGTAATAACTTCGATAGATGGTCATGCCAGACGCCATCTAGAACAGTACA
2359/152   TCAACAGAATGGTAATAACTTCGATAGATGGTCATGCCAGACGCCATCTAGAACAGTACA CBS 1065   GCACGTTGAAGAAAGGTGTGGGGAAAACGCTGTTTCTAGTTCCACCCCAAAAACTCATGA
2359/152   GCACGTTGAAGAAAGGTGTGGGGAAAACGCTGTTTCTAGTTCCACCCCAAAAACTCATGA
                  Mig1 →
CBS 1065   CTCCACCCGGTCTCTTTCAAGGTGTATCTTGTCTAGCATAACATCAAACAGATAGTCATA
2359/152   CTCCACCCGGTCTCTTTCAAGGTGTATCTTGTCTAGCATAACATCAAACAGATAGTCATA CBS 1065   TTACTGTCATGTCTGTTCAGCTGGATAAAACTTGCTCAATTGTTAAGTGTTACAAACCAG
2359/152   TTACTGTCATGTCTGTTCAGCTGGATAAAACTTGCTCAATTGTTAAGTGTTACAAACCAG
                                                 CAAT box
CBS 1065   GACCAGAAAGATTATA-AAAAAGCGTTATTCCAAAGGTATGACAGGACGATCGCTGCAAG
2359/152   GACCAGAAAGATTATTTAAAAAGCGTTATTCCAA-GGT-TGACAG--CGTACGCTGCAAG
                   New TATA box created
```

```
CBS 1065   AAAAA-------------------------------------------ATAAGAGAGAATAGACT
2359/152   AAAAAGCGTTATTCCAAGGTTGACAGCGTACGCTGCAAGAAAAATAAGAGAGAATAGAC-
                              Repeat Region
CBS 1065   CAAACAGATCGAAACGTTAAGCGCAAAAAAACATCAAGTATG
2359/152   C-AAC-GATCGA--CGTTAAGCGCAAAAAA-CTACAAGTATG
           Trxn start
```

FIG. 4B

KLUYVEROMYCES LACTIS MALTASE/MALTOSE PERMEASE BI-DIRECTIONAL PROMOTER AND USE THEREOF

FIELD OF THE INVENTION

The present invention relates to the field of molecular biology and more particularly to a novel DNA sequence possessing regulated transcriptional promoter activity in two directions, to expression vectors containing this sequence, and to their use for the production of recombinant proteins from either homologous or heterologous sources. The invention also relates to the recombinant cells containing this DNA sequence.

BACKGROUND OF THE INVENTION

Model bacterial species, such as *Escherichia coli*, have been used in important molecular biological processes such as the amplification of desirable nucleic acid sequences and the production of heterologous gene products. Unfortunately the ability of bacteria to make functional products from eukaryotic genes is often limited due to alternate prokaryotic codon biases, improper protein folding, and divergent pathways of secondary modifications such as protein glycosylation. For this reason many researchers have turned their attention to yeast species, some of which have been found to be suitable hosts for the expression of proteins of eukaryotic origin.

Yeasts are more easily cultured than cells of many higher eukaryotes and lend themselves to genetic manipulations commonly performed with prokaryotes yet have the capacity for complex post-translational modifications including glycosylation events, proteolytic maturation, and disulphide bond formation (Eckart and Bussineau 1996). Traditionally *Saccharomyces cereviseae* has been used for this production but in recent years focus has shifted to other yeast species, including the dairy yeast *Kluyveromyces lactis*, which has become a model system of studies on the molecular physiology of "non-conventional" yeasts (Breunig et al 2000, Flores et al 2000). One of the difficulties with *S. cereviseae* as a production system is its preference for fermentation under aerobic conditions. This is known as the Crabtree effect. The Pasteur effect is the opposite: the repression of fermentation in aerobic conditions (Breunig et al 2000).

Crabtree-positive yeasts need to be cultured under sugar limited conditions to prevent the decarboxylation of pyruvate to ethanol. Such conditions typically result in low rates of growth and protein synthesis (Breunig et al 2000). If *S. cereviseae* is not grown under sugar-limited conditions, each molecule of pyruvate that is reduced to ethanol is not available to the TCA cycle again resulting in reduced biomass yields and ATP production (Schaffrath and Breunig 2000).

*Kluyveromyces lactis*, like many yeast species, differs from *S. cereviseae* in that it prefers respiration as opposed to fermentation under aerobic conditions. Under aerobic conditions *K. lactis* oxidizes pyruvate to $CO_2$ through the TCA cycle and therefore produces more ATP and reducing equivalents per molecule of pyruvate (Flores et al 2000). Besides relief from the Crabtree effect *K. lactis* possesses a number of other attributes that make it an attractive host for the expression of heterologous proteins. As a naturally occurring dairy yeast, *K. lactis* is generally regarded as a safe organism and has been considered a food grade organism by the US FDA. It has excellent fermentative characteristics and can be cultured at high cell densities (>100 g dry cell weight/l) making it amenable to large-scale industrial applications.

Genetic tools have been developed to make use of Kluyveromyces as a host system for the production of recombinant proteins. Several heterologous gene expression systems have been successfully developed for *K. lactis* making this organism an attractive alternative for heterologous gene expression in industrial applications. *Kluyveromyces lactis* is capable of using many of the vectors, promoters and marker genes already used in *S. cereviseae* systems however these have not been optimized for *K. lactis*. With the exception of natural promoters for the 3-phospoglycerate kinase (U.S. Pat. No. 5,646,012), RP28 ribosomal protein (U.S. Pat. No. 5,627,049), alcohol dehydrogenase (U.S. Pat. No. 5,624,046), transaldolase (U.S. Pat. No. 5,616,474) and pyruvate decarboxylase (U.S. Pat. No. 5,631,143) genes no other endogenous promoters have been developed for expression in *K. lactis*. The rate at which an introduced gene will be transcribed depends not only on the nature of the gene but also on the promoter associated with the gene. The selection of the appropriate promoter is therefore crucial for efficient heterologous protein expression. Certain applications favor the use of strong constitutive promoters to drive gene expression while other applications require promoters that can be externally regulated to give a phased expression. Regulated expression is particularly useful for the expression of products that may be toxic to the host organism.

Fermentation conditions can be controlled such that the toxin is not produced while host cell biomass is increased. This is commonly achieved by the use of glucose as a major carbon source due to its ability to suppress the expression of genes necessary for the utilization of alternate carbon sources (Dong and Dickson 1997). Regulated expression can be achieved by utilizing promoters derived from one of these alternate pathways. Many of the proteins involved in this type of carbon catabolite repression have been identified in *S. cereviseae* and most are believed to have functional analogues in *K lactis*.

The Saccharomyces ScSNF1p kinase, which has been conserved across many eukaryotic taxa from yeasts, plants and mammals (Dong and Dickson 1997, Carlson 1998), is part of the signal cascade that directs a coordinated response to changing glucose concentrations. One of the targets of ScSNF1p is Mig1p, a DNA-binding transcriptional repressor of many glucose-repressed genes (Lutfiyya and Johnston 1996, Hu et al 1999, Breunig et al 2000). Mig1p binds to conserved GC-elements present in the promoters of glucose-repressed genes and disruption of Mig1p gene function results in dramatic de-repression of expression (Wang et al 1997, Zaragosa et al 2000). *Kluyveromyces lactis* possess a Mig1p homologue (KlMig1p) responsible for the repression of the glucose-repressed lactose-galactose regulon (Dong and Dickson 1997, Hu et al 2000). De-repression is not complete in the absence of KlMig1p suggesting the presence of an additional KlMig1p independent pathway and regulation by other repressors (Dong and Dickson 1997). Glucose repressed genes in alternative sugar metabolism also involve transcriptional activator proteins. In Saccharomyces, Gal4p is a transcriptional activator of many glucose-repressed genes and is turn repressed by Gal80p. This secondary repression is relieved by raised intracellular concentrations of non-glucose sugars (Hu et al 2000). The *K. lactis* homologue KlGal4p (also called Lac9p) escapes inhibition by KlGal80p and is thought to activate its own expression, thereby increasing the concentration of the activator. The concentration of KlGal4p (Lac9p) limits expression of many glucose repressed regulons. In addition to KlMig1p and KlGal4p(Lac9p) there are other transcription factors, many of which are yet to be identified, that add specificity to each of the regulated alternate pathways.

The selection of an appropriate promoter is crucial for efficient heterologous protein expression. Although relatively rare, bi-directional promoters are generally believed to regulate related gene products that are produced in stoichiometric quantities (Levine et al 1992, Menne et al 1994). An artificial construct utilizing the bi-directional expression of the reporter genes gusA and lacZ, driven by the promoter of a-aminoadipyl-cysteinyl-valine [ACV] synthetase/isopenicillin N-synthetase from *Acremonium chrysogenum*, has shown that the pcbC promoter (isopenicillin N-synthetases) was at least 5 times stronger than pcbAB (ACV synthetase) promoter (Menne et al 1994).

References Cited

Breunig K D, Bolotin-Fukuhara M, Bianchi M M, Bourgarel D, Falcaone C, Ferrero I, Frontali L, Goffrini P, Krijger J J, Mazzoni C, Milkowski C, Steensma HHY, Wesolowski-Louvel M, Zeeman AM. 2000. Regulation of primary carbon metabolism in *Kluyveromyces lactis*. Enzyme and Microbial Technology 26:771–780.

Carlson M. 1998 Regulation of glucose utilization in yeast. Current Opinions in Genetics and Development 8:560–564.

Dong J, Dickson R C. 1997 Glucose represses the lactose-galactose regulon in *Kluyveromyces lactis* through a SNF1 and MIG1-dependent pathway that modulates galactokinase (GAL1) gene expression. Nucleic Acids Research 25:3657–3664.

Eckart M R, Bussiiineau C M. 1996. Quality and authenticity of heterologous proteins synthesized in yeast. Current Opinions in Biotechnology 7:525–530.

Flores C-L L, Rodriguez C, Petit T, Gancedo C. 2000. Carbohydrate and energy-yielding metabolism in non-conventional yeasts. FEMS Microbiology Reviews 24:507–529.

Gancedo J M. 1998. Yeast carbon catabolite repression. Microbiology and Molecular Biology Reviews 62:334–361.

Geber A, Williamson P R, Rex J H, Sweeney E C, Bennett J E. 1992. Cloning and characterization of a *Candida labicans* maltase gene involved in sucrose utilization. Journal of Bacteriology 174:6992–6996.

Hong S H, Marmur J. 1986. Primary structure of the maltase gene of the MAL6 locus of *Saccharomyces carlsbergensis*. Gene 41:75–84.

Hu Z, Zue Y, Jiang H, Sherwood P W, Michels C A. 2000. Analysis of the mechanism by which glucose inhibits maltose induction of MAL gene expression in Saccharomyces. Genetics 154:121–132.

Levine J, Tanouye L, Michels C A. 1992. The $UAS_{MAL}$ is a bidirectional promoter element required for the expression of both the MAL61 and MAL62 genes of Saccharomyces MAL6 locus. Current Genetics 22:181–189.

Lundin M, Mehlin J O, Ronne H. 1994. Importance of a flanking AT-rich region in target site recognition by the GC box-binding zinc finger protein MIG1. Molecular and Cellular Biology 14:1979–1985.

Lutfiyya L L, Johnston. 1996. Two zinc-finger-containing repressors are responsible for glucose repression of SUC2 expression. Molecular and Cellular Biology 16:4790–4797.

Menne S, Walz M, Kuck U. 1994. Expression studies with the bidirectional pcbAB-pcbC promoter region from *Acremonium chrysogenum* using reporter gene fusions. Applied Microbiology and Biotechnolog 42:57–66.

Punt P J, Oliver R P. Dingemanse M A, Pouwels P H, van den Hondel C A. 1987. Transformation of Aspergillus based on the hygromycin B resistance marker from *Escherichia coli* Gene 56:117–124.

Schaffrath R, Breunig K D. 2000. Genetics and molecular physiology of the yeast *Kluyveromices lactis*. Fungal Genetics and Biology 30:173–190.

Wang J, Needleman R. 1996. Removal of a Mig1p binding site converts a MAL63 constitutive mutant derived by interchromosomal gene conversion to glucose insensitivity. Genetics. 142:51–63.

Wang J, Sirenko O, Needleman R. 1997. Genomic footprinting of Mip1P in the MAL62 promoter. Journal of Biological Chemistry 272:4613–4622.

Zaragoza O, Rodriguez C, Gancedo C. 2000. Isolation of the MIG1 gene from *Candida albicans* and effects of its disruption on catabolite repression. Journal of Bacteriology 182: 320–326.

SUMMARY OF THE INVENTION

In accordance with the instant invention, what has been identified, cloned and sequenced is a region of the *K. lactis* genome having regulated transcriptional promoter activity [SEQ ID NO: 1]. This sequence was obtained by screening a total genomic library of *K. lactis* with a probe derived by reverse genetics of a highly expressed gene product followed by sequence analysis of the entire gene locus. More specifically the region shown in [SEQ ID NO: 1] corresponds to the promoter of the *K. lactis* maltase gene and may be used for the efficient production of recombinant proteins in yeasts of the Kluyveromyces genus and may also be used in other host organisms.

Moreover analysis of a larger region of the Kluyveromyces genome, immediately flanking [SEQ ID NO: 1], has identified two reading frames in opposite directions; one corresponding to the maltase gene and the other corresponding to the maltose permease gene. This unexpected discovery demonstrates that the complementary strand of the region presented in [SEQ ID No: 1] also possesses promoter activity acting in the opposite direction [SEQ ID NO: 2].

One aspect of the present invention involves the DNA sequence comprising the sequence presented in [SEQ ID NO: 1], or a sequence of its complementary strand presented in [SEQ ID NO: 2], or derivatives thereof which possess promoter activity.

Derivative is understood to mean any sequence obtained from the sequences given in [SEQ ID NO: 1] and [SEQ ID NO: 2], by structural modifications (mutations, additions, deletions, substitutions) which conserve or modify promoter activity in either direction. In particular, the mutations may involve one or more nucleotides and the additions, deletions, or substitutions may involve regulatory elements or binding sites for positive activators.

Another aspect of the present invention relates to a recombinant DNA comprising a DNA sequence as defined above. This recombinant DNA may contain the promoter sequence, or a derivative thereof, in which one or several restriction sites have been advantageously inserted, or to which a multiple cloning site has been added, to facilitate the insertion of one or more structural genes.

More preferably, the recombinant DNA contains signals permitting the sub-cellular targeting, surface localization, or secretion of the expression products of said structural genes.

In a specific embodiment of the invention, the recombinant DNA is part of an expression plasmid that may be autonomously replicating or integrative in nature.

In particular, autonomously replicating vectors may be ideally obtained by using autonomously replicating sequences (ARS) in the host selected. In *K. lactis* replication origins from known plasmids (such as pKDI) or a novel ARS may be advantageously involved.

Integrative vectors may be obtained by using homologous sequences corresponding to certain regions of the host genome which permits targeting of the vector to a specific locus by integrative recombination.

Another aspect of the present invention relates to recombinant cells that contain at least one of the DNA sequence as defined above.

For such purpose, Cells are chosen preferably from yeasts of the Kluyveromyces genus however it is understood that the invention is applicable to all recombinant cells, including but not limited to all yeasts and filamentous fungi, in which the promoter regions of the invention are active.

These cells may be obtained by any one of well known methods for enabling a foreign DNA to be introduced into a cell. For example, this may be accomplished by cell protoplast transformation, electroporation, ballistic gene delivery or any other technique known to a person skilled in the art.

Another aspect of the invention relates to the use of the sequence as defined above for the expression of recombinant genes. In particular, it is possible to use these sequences to simultaneously drive the expression of several genes.

Advantageously, the invention permits the use of the bi-directional promoter for the simultaneous expression of recombinant genes in opposite directions. These genes may be tandemly linked as fusion proteins in a single direction and two sets of genes may be expressed in opposite directions.

Advantageously, one of the genes may encode an easily assayed reporter while the other gene may encode a product for which no assay exists. Expression levels of the easily assayed reporter can be used to assess the relative expression of the partnered gene.

Advantageously, one of the genes may encode a positive activator for the enhanced transcription from the opposite promoter such that cellular levels of positive activator for the optimal expression from the opposite promoter are not limiting.

Advantageously, the sequences of the invention may be used for the expression of genes encoding proteins of interest in the industrial enzyme, pharmaceutical, or foodstuffs sectors. By way of example, there may be enzymes such as polygalacturonase, xylanase, phytase, superoxide dismutase, catalase, amylase, cellulases, chitinase, and chymosin, N-glycan processing enzymes such as mannosidase, mannosyl transferase, N-acetyl glucososaminyl transferase, galactosyl transferase, and sialyl transferase, hydrophobic polypeptides such as cerato-ulmin, hydrophobin a and b, lymphokines such as interleukins, interferons, and colony stimulating factors, growth factors such as growth hormones, erythropoietin, FGF, EGF, and TGF, antigenic polypeptides for the production of vaccines or alternately polypeptide fusions of portions of antigenic polypeptides with stabilizing molecules.

BRIEF DESCRIPTION OF THE SEQUENCES AND THE FIGURES

SEQ ID NO: 1: Nucleotide sequence of the 1069 bp region of the chromosomal fragment upstream of but not including the initiation codon for translation of the *K. lactis* maltase gene having promoter activity.

SEQ ID NO: 2: Nucleotide sequence of the 1069 bp region of the chromosomal fragment upstream of the initiation codon for translation of the *K. lactis* maltose permease gene having promoter activity. This sequence is the reverse complement of [SEQ ID NO: 1].

SEQ ID NO: 3: Degenerate oligo nucleotide forward primer for the amplification of the maltase gene fragment from genomic DNA of *K. lactis*.

SEQ ID NO: 4: Degenerate oligo nucleotide return primer for the amplification of the maltase gene fragment from genomic DNA of *K. lactis*.

SEQ ID NO: 5: Oligonucleotide forward primer for the inverse PCR amplification of the maltase/maltose permease gene locus.

SEQ ID NO: 6: Oligonucleotide return primer for the inverse PCR amplification of the maltase/maltose permease gene locus.

SEQ ID NO: 7: Oligonucleotide forward primer for the construction of the basic expression cassette. The primer was designed for the tailed PCR amplification of the maltase/maltose permease promoter and contained a 5'tail (GGGGCCC) followed by restriction sites for HindIII, a 6 bp spacer, BamHI site followed by 27 bp of sequence directed to the promoter.

SEQ ID NO: 8: Oligonucleotide return primer for the construction of the basic expression cassette. The tailed primer directed the construction of a multiple cloning sites composed of restriction enzyme recognition sites for KpnI, NheI, PacI and SphI at terminus of the maltase promoter. The SphI site contained the ATG start codon of the reporter gene to be transcribed in the maltase direction.

SEQ ID NO: 9: Oligonucleotide forward primer for the re-engineering of the endopolygalacturonase gene for insertion into the basic expression cassette.

SEQ ID NO: 10: Oligonucleotide return primer for the re-engineering of the endopolygalacturonase gene.

SEQ ID NO: 11: Oligonucleotide forward primer for the construction of the bi-directional fluorescent marker cassette. The tailed primer directed the addition of restriction enzyme recognition sites for AflII, NheI and BamI at the terminus of the maltose permease promoter for the in-frame insertion of yellow fluorescent protein EYFP.

SEQ ID NO: 12: Oligonucleotide return primer for the construction of the bi-directional fluorescent marker cassette. The tailed primer directed the addition of restriction enzyme recognition sites for NotI, BglII and BamI at the terminus of the maltase promoter for the in-frame insertion of cyan fluorescent protein CFP.

SEQ ID NO: 13: Partial maltase polypeptide sequence for *K. lactis*.

SEQ ID NO: 14: Maltase polypeptide sequence for *Saccharomyces carlsbergensis*.

SEQ ID NO: 15: Maltase polypeptide sequence for *Saccharomyces cereviseae*.

SEQ ID NO: 16: Maltase polypeptide sequence for *Candida labicans*.

SEQ ID NO: 17: Partial maltase/maltose permease promoter region from *K. lactis* 2359/152 (Accession No. AJ007636).

SEQ ID NO: 18: N-terminal region of *K. lactis* maltase polypeptide.

SEQ ID NO: 19: Partial degenerate maltase N-terminal peptide sequence.

SEQ ID NO: 20: Partial well-conserved region of a maltase peptide.

SEQ ID NO: 21: Nucleic acid sequence of a Saccharomyces bi-directional promoter.

SEQ ID NOS: 22 and 23: Partial nucleic acid sequence of a *K. lactis* maltose pennease promoter.

SEQ ID NO: 24: Nucleic acid sequence of a Gal4 binding sequence.

FIG. 1: Proteins secreted into the culture filtrate late in the fermentation of CBS 1065 transformed with lac-driven cellulase. While the production of cellulase could not be detected by SDS-polyacrylamide electrophoresis, there was a high level of production of a 68 kDa polypeptide in the presence of YP+glycerol (lane 1), YP+raffinose (lane 2) and YP+glucose (lane 3). The expression of the 68 kDA polypeptide was suppressed in the presence of galactose. Expression of the protein was suppressed in cultures grown in YP+glycerol+galactose (lane 4) and YP+glucose+galactose (lane 6) and to a lesser extent when grown in YP+raffinose+galactose (lane 5). The sizes of molecular weight markers (Kda.) are given at the left of the figure.

FIG. 2: Multiple sequence alignment of the maltase polypeptide sequences for *K. lactis* (partial) (SEQ ID NO: 13), *Saccharomyces carlsbergensis* (SEQ ID NO: 14), *Saccharomyces cereviseae* (SEQ ID NO: 15), and *Candida labicans* (SEQ ID NO: 16).

FIG. 3: Schematic map of the MAL locus of *K. lactis* CBS 1065. The maltase and maltose permease genes are transcribed in opposite directions from a common promoter region. The positions of the BglII sites used for the inverse PCR amplification of the maltose permease, the bi-directional promoter, and a portion of the maltase gene are indicated.

FIG. 4: Sequence comparison of the maltase/maltose permease promoter region from *K. lactis* CBS1065 (SEQ ID NO: 1) and 2359/152 (Accession No. AJ007636)(SEQ ID NO: 17). Single base-pair changes are indicated in bold. The TATAAA box of the CBS1065 maltase promoter sequence, absent from the 2359/152 sequence, and its matching CAAT box are double underlined. Putative regulatory elements are underlined in bold.

Figure 5:
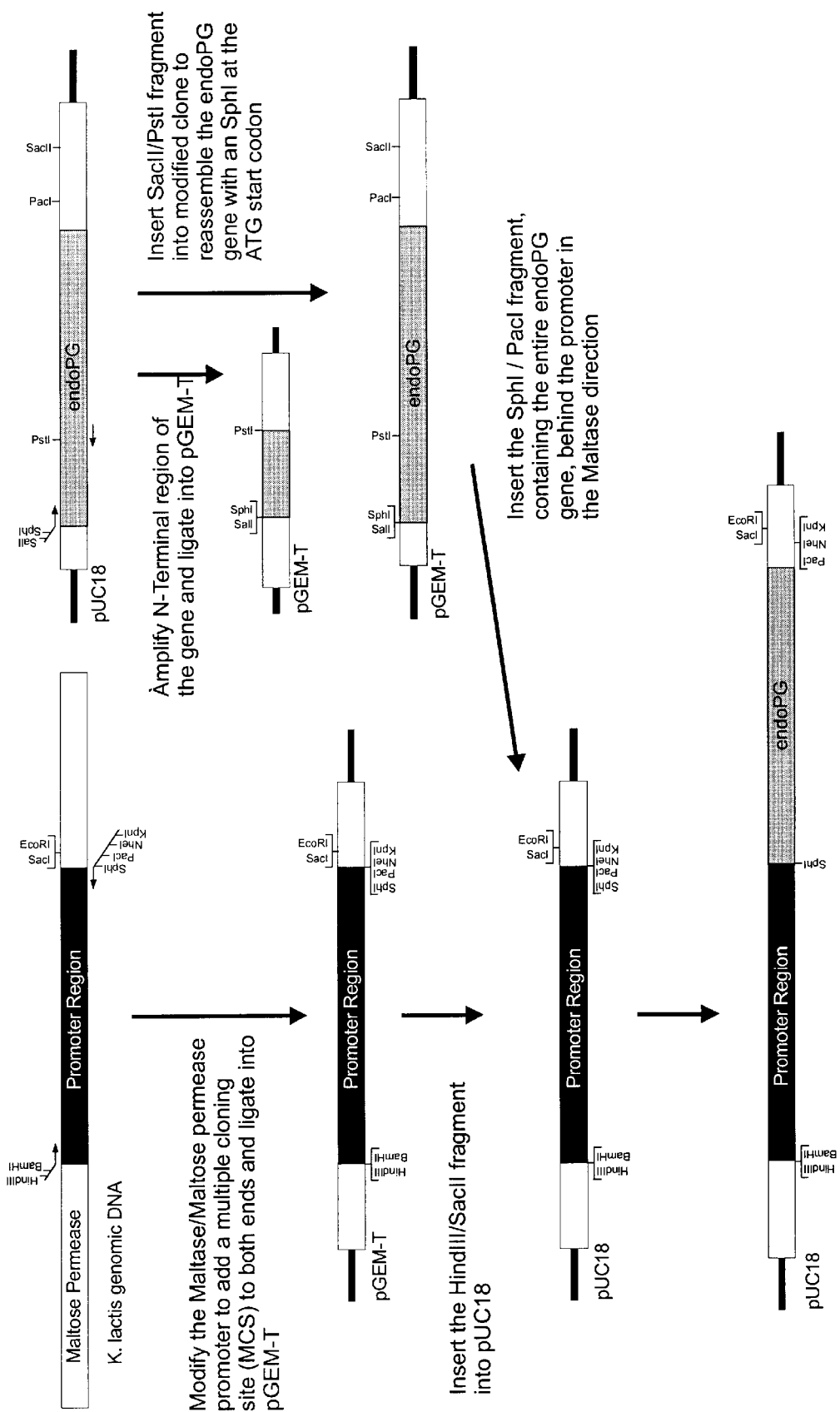

FIG. 5: Construction of endopolygalacturonase expression cassette. The tailed primers directed the incorporation of restriction sites in a multiple cloning site (MCS). The endoPG gene of *Opphiostoma novo-ulmi* was modified to incorporate an SphI site at the ATG start codon and inserted behind the maltase promoter.

Figure 6:
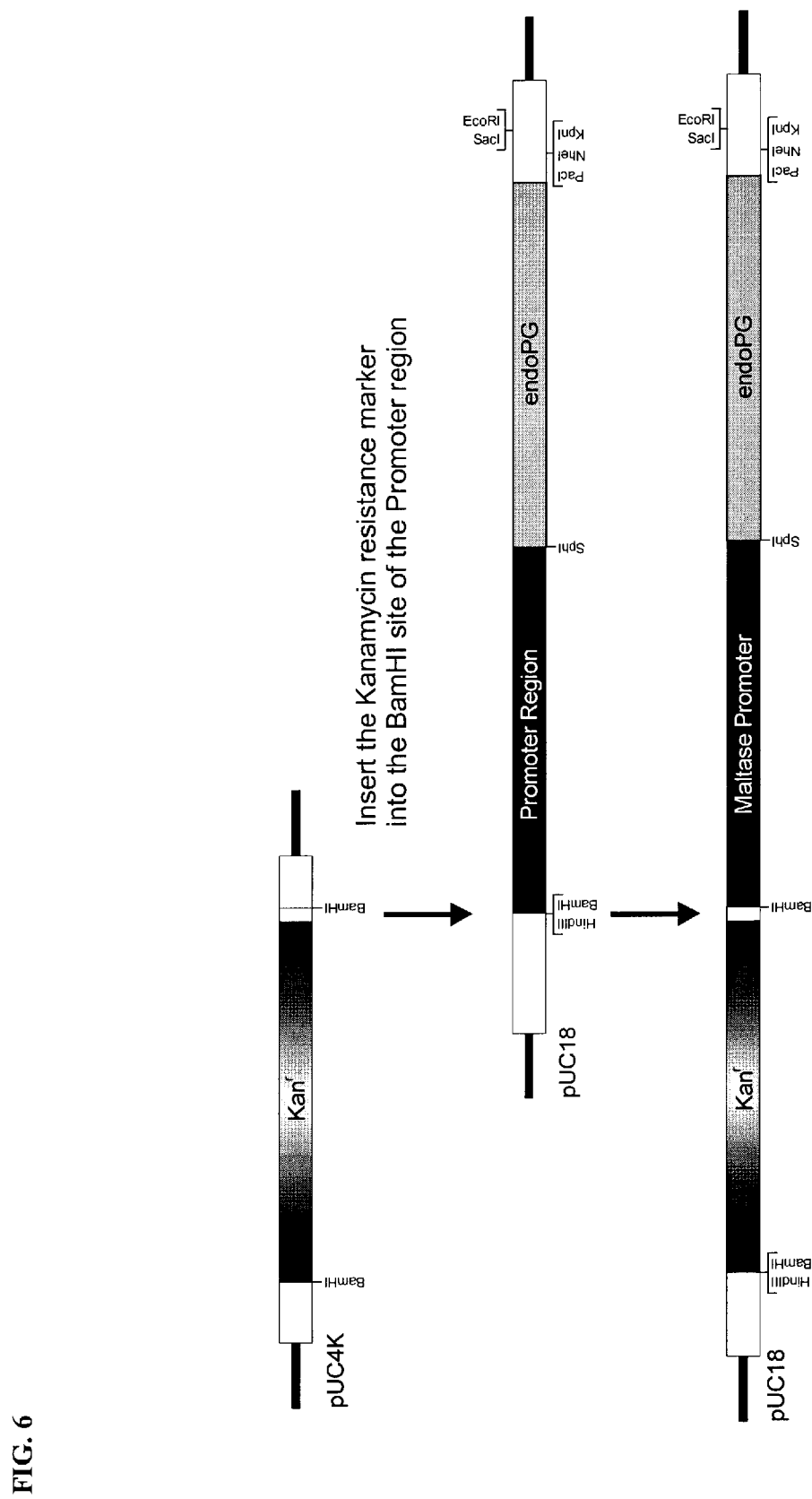

FIG. 6: Insertion of a dominant selectable marker into the endoPG expression cassette. The kan^r gene was inserted into the BamHI site located behind the maltase permease promoter. The direction of transcription is the same as for the maltase permease but is driven by the lacZ promoter.

Figure 7:
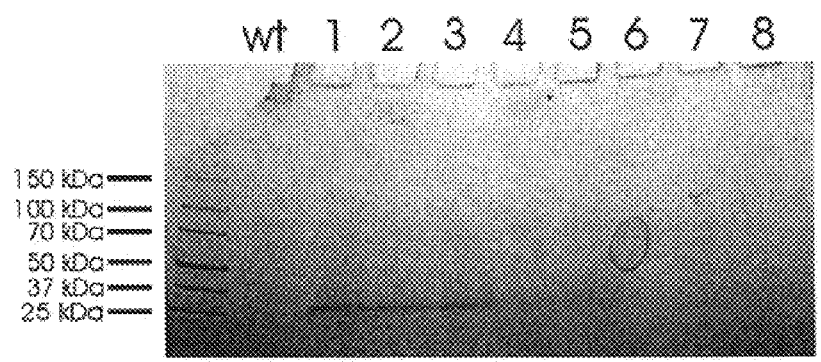

FIG. 7: *Kluyveromyces lactis* co-transformed with the endoPG expression vector and the hygromycin resistance vector (pAN7–1). The negative control (non-transformed wild-type) can be seen in first lane (wt). Of the eight transformants shown, three are expressing a protein which co-migrates with endoPG. Size standards (kDa.) are to the left of the gel FIG. 8: Construction of a bi-directional expression cassette for the simultaneous expression of cyan fluorescent protein (ECFP) and yellow fluorescent protein (EYFP) in *K. lactis*.

DETAILED DESCRIPTION AND BEST MODE

This invention will be more completely described by means of examples which should be considered as illustrative and non-limiting.

EXAMPLES

Example 1

Isolation of the Promoter Region of the *K. lactis* Maltase Gene

During routine expression of plasmid-borne non-integrative cassettes in *Kluyveromyces lactis*, an abundantly secreted protein was observed late in the fermentation protocol (FIG. 1). The presence of the protein was unexpected and was originally thought to be due to the expression cassette. The protein was purified and the peptide sequence was determined for two regions of the protein. The N-terminal region was determined to be TITKEVSEHPQT-DPKWWKEA (SEQ ID NO: 18). Following proteolytic cleavage the sequence of an internal peptide fragment was determined to be NAIYESAVGFWLDHGVDGFR (amino acids 30–49 of SEQ ID NO: 13). Comparison of the polypeptide sequence to predicted coding products of the expression cassette revealed that the protein was not encoded by any genes of the expression cassette hence it was assumed to be an endogenous *K. lactis* product. Comparison of the peptide sequence to registered databases suggested that the protein belonged to a family of alpha-glycosidases (maltases). A BLAST search of the NIH databases revealed that the partial peptide sequences shared a high degree of homology with the alpha-glycosidase (maltase) genes of the fungal species *Saccharomyces cereviseae* (P07265; Hong and Marnur 1986), *S. carlsbergensis* (M12601; Hong and Marmur 1986), and *Candida labicans* (M94674; Geber et al 1992) (FIG. 2). Sequence alignments of these sequences revealed conserved regions that could be indicative of common functional domains hence the protein was identified as a *K. lactis* maltase gene product.

Degenerate primers (SEQ ID NOS: 3 and 4) were designed by reverse genetics according to the partial N-terminal peptide sequence HPQTDDKWWKE (SEQ ID NO: 19) and to a well-conserved region of the aligned maltase sequences QDDLNWENEDL (SEQ ID NO: 20) having low codon redundancy. Amplification products from *K. lactis* genomic DNA were sequenced and a 555 bp fragment of the maltase gene was authenticated by alignment with the other reported maltase genes listed above. Two regions of this amplified DNA, internal to the original priming sites, were used to design a second set of outward directed primers for the inverse PCR amplification of genomic DNA of *K. lactis* [SEQ ID NO. 5 AND SEQ ID NO. 6]. Genomic DNA was digested with BglII, religated at a low DNA concentration (1.0 μg/ml) and the circularized DNA was amplified using the second set of outwardly directed primers. The resultant amplification product was found to encode the N-terninal region of the maltase gene and the maltose permease gene separated by a common promoter region (FIG. 3).

The PCR-derived sequences were then used to screen a lambda DNA library of *K. lactis* genomic DNA sequences. The library was constructed following the ligation of partially digested genomic DNA fragments (10–20 Kb MboI) into the BamHI site of EMBL-3 arms and packaging the recombinant phage using a commercially available system. A recombinant clone was recovered that contained the entire maltase gene on >10 Kb BamHI fragment. Further sequence analysis of the maltase locus revealed that in addition to encoding the entire maltase gene it contained a 1069 bp upstream promoter region as well as a coding region having similarity to the *S. cereviseae* maltose permease (MAL61) gene (Levine et al 1992). Similar to the *S. cereviseae* gene cluster, the *K. lactis* maltase and maltose permease genes were oriented in opposite directions and shared a common promoter region (FIG. 3).

Since the promoter operates bi-directionally, the sequences of the upper and lower strands were aligned to check for common sequences. Since genes responsible for the transcription of components of the same pathway are often coordinately regulated (Carlson 1998), the maltase and maltose permease genes may be repressed by the same transcription factors operating in the same relative parts of the promoter. Alternately, there may exist individual sites on one or the other of the strands that regulate expression independently. The evidence from sequence analysis suggests putative binding sites for known carbon catabolite repressors Mig1 and Lac9, as well as a region with sequence similarity to the $UAS_{MAL}$ of Saccharomyces. Sequence alignment also suggests that several of these sites are in similar positions relative to their respective start sites for both the maltase and maltose permease genes.

The *K. lactis* promoter was searched for regions having similarity to the $UAS_{MAL}$ of the bi-directional promoter of Saccharomyces which has two 11-basepair repeats of GAAA(A/T)TTTCGC (SEQ ID NO: 21) located at −515 to −525 (copy I) and −566 to −576 (copy II) relative to the initiation codon (ATG) of the *S. cereviseae* maltose permease gene. The entire $UAS_{MAL}$ is contained within the region −515 to −582 upstream of the ATG (Levine et al 1992). Sequences exhibiting similarity to the repeats were found at positions 511 to 522 and 614 to 625 in [SEQ ID NO. 1], (FIG. 4). The sequence GAAATTTTCCT (SEQ ID NO: 22) was located at −551 to −522 upstream of the *K. lactis* maltose permease initiation codon while the sequence GAAATTTTCTC (SEQ ID NO: 23) was further upstream at positions −614 to −625. While these sequences were further apart from each other (103 vs 51 bp) than those in Saccharomyces (Levine et al 1992), they likely still represent the $UAS_{MAL}$ site. DNAase footprinting in Saccharomyces determined that copy II is the primary activation element and may be acting alone or cooperatively with copy I. Copy II in the *K. lactis* sequence was found to be in the same relative position as copy II in Saccharomyces.

The repressor region between −583 to −638, associated with the $UAS_{MAL}$ of Saccharomyces, was not found in the *K. lactis* promoter. This may be due a greater degree of sequence divergence of a functionally equivalent sequence in *K. lactis* compared to its Saccharomyces counterpart (Levine et al 1992). An analogous sequence may also be absent and repression may be due to other unidirectional elements that compete with the activator and prevent its binding (Wang et al 1997).

One such repression element, found in the Saccharomyces bidirectional MAL61–MAL62 promoter, is Mig1p. This regulatory protein is a $C_2H_2$ zinc finger protein able to bind to promoters of several genes repressed by glucose (Lutfiyya and Johnston 1996, Gancedo 1998) and requires a GC-rich box (G/C)(C/T)GGGG in addition to an AT rich region flanking the element on the 5' side (Lundin et al 1994, Gancedo 1998). Three potential Mig1p binding sites were identified in the maltase direction [SEQ ID NO: 1] at positions 265 to 278, 398 to 412, and 778 to 792 (FIG. 4). One potential Mig1p binding site was identified in the permease direction [SEQ ID NO: 2] at position 683 to 696. Disruption of MIG1 has been found to relieve glucose repression and increase maltase expression 40–60 fold in *S. cereviseae* (Hu et al 1995). The removal of a single Mig1p binding site from the bidirectional MAL63 promoter has also been shown to relieve glucose repression of MAL genes in Saccharomyces, while the addition of a site can bring glucose insensitive mutants back under repression (Wang and Needleman 1996). *Kluyveromyces lactis* has been shown to contain a homologue of the *S. cereviseae* MIG1 gene that is expected to carry out similar regulatory functions (Breunig et al 2000). The Mig1p binding sites found in *K. lactis* therefore are presented as promising targets for modification in order to relieve glucose repression from this promoter.

Lactose metabolism is inducible by Lac9p in *K. lactis*, a functional analogue of the well-characterized Gal4p activator of *S. cereviseae*. The expression of the lactose-galactose operon is induced by lactose or galactose but repressed by glucose. When glucose is present, the Lac9p positive activator is prevented from binding regulatory elements in the bi-drectional promoter shared by KlLAC4 (b-galactosidase) and KlLAC12 (lactose permease). Lac9p possesses a $Zn_2Cys_6$ DNA binding domain which binds to a consensus sequence homologous to the Gal4binding sequence CGGA(G/C)GACAGTC(C/G)TCCG (SEQ ID NO: 24). The *K. lactis* gal genes are very sensitive to the expression levels of Lac9p and can vary 100 fold in expression. When glucose is present, the Lac9 positive activator is prevented from binding regulatory elements in the bi-directional promoter shared by KlLAC4 (β-galactosidase) and KlLAC12 (lactose permease). In the promoter sequence of the present invention three regions were similar to the Lac9p binding site corresponding to positions 226 to 242 in the maltase direction [SEQ ID NO: 1] as well as positions 680 to 696 and 828 to 844 in the permease direction [SEQ ID NO: 2] (FIG. 4). This promoter may therefore be activated by lactose or galactose when glucose is not repressing expression.

Putative transcription start sites were located 39 bp upstream of the coding region in the maltase promoter [SEQ ID NO: 1] at positions 1031 to 1036 (CAAACA), and 23 bp upstream of the coding region in the maltose permease promoter [SEQ ID NO: 2] at positions 1046 to 1051 (ACAACA). The putative TATAAA box for the maltase promoter was located 107 bp upstream of the coding region at positions 962 to 967 with a CAAT box separated by 33 bp further upstream at positions 926–929 [SEQ ID NO: 1] (FIG. 4). In the maltose permease direction the TATAAA box was located 56 bp upstream of the translation start site at positions 1013 to 1018 [SEQ ID NO: 2] with a matching CAAT box at positions 958 to 961 a further 52 bp upstream. A 10 bp palindromic sequence was located midway through the bi-directional promoter at positions 490 to 499 [SEQ ID NO: 1] (FIG. 4). Present in roughly the same relative area of both promoters was a TTTGTTTT inverted repeat at position 672 to 679 in [SEQ ID NO: 1] and positions 665 to 672 in [SEQ ID NO: 2] (FIG. 4).

Subsequent to the identification of the MAL locus in *K. lactis* (CBS 1065), a research group headed by A. Dominguez at the Department of Microbiology and Genetics, University of Salamanca, Spain reported the sequence of the MAL locus for *K. lactis* (Strain 2359/152) Accession No: AJ007636. This unpublished sequence confirmed our assignment of the maltase and maltose permease genes however there were significant differences between the two sequences, especially in the promoter region. In addition to several single base-pair changes, indicated on FIG. 4, the 2359/152 sequence carried a 38 bp direct repeat immediately following the transcription start site in the maltase direction. This repeat was absent from the promoter sequence of the present invention. More significantly there were differences between the two sequences in the region of the proposed TATAAA box for our sequence. The 2359/152 carried a TATTTA sequence in place of the TATAAA sequence found in the CBS 1065 sequence. This could directly impact on the rate of transcription of the maltase gene. There were only minor differences in the putative binding sites for the regulatory elements. The inverted repeats, palindromic sequence and UAS were identical between the two sequences (FIG. 4)

Example 2

Construction of an Expression Vector for the Production of Heterologous Proteins To assess the feasibility of using this promoter for the production of heterologous proteins, the maltase/maltose permease promoter was re-engineered to permit the introduction of reporter genes in the maltase direction. Oligonucleotide primers were designed to re-engineer the maltase/maltose permease promoter such that the maltase promoter would drive expression of the endopolygalacturonase I (endoPG) gene of the filamentous fungus *Opphiostoma novo-ulmi* (Accession Number AF052061). The aminoglycoside 3'-phosphotransferase gene from transposon Tn903, conferring resistance to kanamycin (Kan$^r$), was inserted upstream of the promoter to serve as a selectable marker. The primers were tailed such that HindIII and BamHI sites were added to the maltose permease end of the promoter and a SphI, PacI, NheI, KpnI polylinker was added to the maltase end of the promoter. The SphI site contained the ATG start codon for any reporter proteins to be added to this generalized expression cassette. The engineered promoter was amplified from genomic DNA of *K. lactis* CBS 1065 using tailed primers [SEQ ID NO: 7, SEQ ID NO: 8] and the fragment was cloned into pGEM-T vector via TA ligation (Promega). Following sequence confirmation of the recombinant plasmid, the amplified DNA plus a small region of the multiple cloning site was moved into the plasmid pUC18 via directional cloning utilizing the engineered HindIII site in the promoter and the SacI site in pGEM-T (FIG. 5). Successful insertion was confirmed through HindIII/SacI and PacI/SphI digests and comparison of the resultant restriction patterns to the predicted patterns. A restriction site map of the engineered promoter illustrating the relative positions of the engineered sites was called pUC18-MP (FIG. 5).

The insertion of the endopolygalacturonase gene (epgA) behind the maltase promoter required a two stage process whereby the N-terminal region of the coding region first needed to be engineered to add an SphI site containing the ATG start codon, followed by ligation of the remainder of the gene into the expression cassette.

Oligonucleotide primers were designed according to the *Opphiostoma novo-ulmi* epgA gene reported by Temple and Hintz (University of Victoria) [SEQ ID NO: 9 and SEQ ID NO: 10]. The tailed forward primer contained a short 5' terminal spacer sequence followed by restriction sites for HindIII, SalI and SphI. The ATG start codon for the epgA gene was contained in the SphI site [SEQ ID NO: 9]. The return primer spanned the natural PstI site found at position 311 of the *O. novo-ulmi* epgA gene and was tailed with a short 5' terminal spacer and an EcoRI site to allow the movement of the remainder of the epgA gene behind the re-engineered linker [SEQ ID) NO: 10]. The 359 bp amplification product, representing the N-terninal coding region of the epgA gene, was cloned into pGEM-T vector (FIG. 5). The 2200 bp PstI fragment of the authentic epgA gene, encoding the C-terminal region of the gene, was ligated into the PstI site of the engineered PCR product. The correct orientation of the PstI fragment was determined by a SphI/PacI double digest, which released the expected 1264 bp fragment. The resulting plasmid contained an SphI site spanning the ATG start codon and a unique PacI site following the transcription terminator (FIG. 5). The re-engineered epgA gene was cut out of pEPG-RE by a SphI/PacI double digest and ligated into the expression vector. Insertion of the re-engineered epgA gene into pKMP was confirmed by a SphI/PacI double digest.

To insert the Kanamycin resistance gene upstream of the maltose pernease promoter, the BamHI fragment from the commercially available plasmid pUC4K (Pharmacia Biotech), containing the entire Kan$^r$gene, was inserted into similarly digest pUC18-MP (FIG. 6).

Insertion of the BamHI fragment was confirmed through BamHI digestion. Since this fragment could insert two ways, the orientation of selected plasmids was determined by HindIII/SacI digestion and plasmids containing the Kan$^r$-gene in the same direction as the maltose permease promoter were selected. These were identified by yielding fragment sizes of 3100, 1844, and 588 bp upon HindIII/SacI digestion. Even though transcription of the Kan$^r$gene was in the same direction as the maltose permease, the Kan$^r$gene was not linked directly to the maltose permease promoter. The Kan$^r$gene carried its own constitutive promoter (lacZ) as a linker between the maltose permease promoter and the coding region of the aminoglycoside 3'-phosphotransferase gene.

The completed expression vector was a 6.3 Kbp, pUC18 based plasmid that contained the maltase/maltose permease promoter from *Kluyveromyces lactis*, driving the expression of the endopolygalacturonase (EndoPG) gene from *Opphiostoma novo-ulmi* and a separately regulated selectable marker for Kanamycin resistance (FIG. 6).

Because of the close proximity of the resistance marker to the maltose permease promoter it was possible that the expression could be down regulated during the initial phases of the transformation procedure. This marker was therefore not used for primary selection of integration of the expression cassette into the host. Protoplasts of *Kluyveromyces lactis* were instead co-transformed with the expression cassette and a plasmid, pAN7-1 (Punt et al 1987), containing the hygromycin resistance gene hph. Transformants were selected on complete media agar (OCM-agar) supplemented with 200 μg/ml hygromycin. Positive transformants were sub-cultured with continued selection and resistant colonies were inoculated into 50 ml of liquid OCM, supplemented with 10 mM maltose. The liquid cultures were grown for 72 hours, at 30° C., in a non-baffled flask on a 150 rpm shaker. Aliquots of the culture were sampled (1.0 ml) and the *K. lactis* cells were removed from the media by centrifugation. 50 μl of the supernatant was separated by electrophoresis through a 4%–20% SDS-PAGE ready-gel from BIO-RAD at 200V for 40 minutes (FIG. 7). The gel was stained for 1 hour with Coomassie Blue R-250 staining solution and then destained for 3 hours.

The predicted molecular weight of fully processed EndoPG protein was 36.15 kDa. The first 25 amino acids, recognized as a putative secretion signal, were removed from the estimation. The size of the protein seen in lanes 1–3 was determined, by standard curve, to be 36.17 kDa suggesting that transformants 1–3 are synthesizing and secreting EndoPG protein (FIG. 7).

Since the negative control (non-transformed) culture did not produce a visible amount of a protein migrating at this distance, it seems likely that expression is due to the expression vector and the maltase promoter. The use of the maltase promoter for the expression of heterologous proteins was therefore validated. The transformants 1–3 were not resistant to Kanamycin suggesting that the aminoglycoside 3'-phosphotransferase gene was not being expressed.

Example 3

Besides the high level of expression from the maltase promoter, this genetic locus offers other advantages for biotechnological applications. To assess the utility of the maltase/maltose permease bi-directional promoter for the simultaneous expression of multiple products an expression cassette was constructed to enable the regulated production of proteins in both directions. This type of expression cassette offers several advantages: (1) Employing a bi-directional promoter allows for the production of two different proteins in known relative amounts. Menne et al (1994) demonstrated that the two cephalosporin genes of *Acremonium chrysogenum* pcbAB and pcbC shared a common bi-directional promoter and that expression of the pcbC was at least five times stronger than the pcbAB promoter. It is likely that the *K. lactis* maltase/maltose permease promoter will not produce these two proteins in the same amount but more likely in some constant ratio. The linkage of these two genes through a common promoter suggests that they are co-regulated. Two reporter genes driven in opposite directions from the maltase/maltose permease directions are expected to be produced in the same relative ratio as the original gene products. (2) By expressing two proteins that can be quantified separately, unique characters of the promoter can be assessed in both directions in a single experiment. Any modifications made to the sequence of the promoter can then be tested for effects on the rate of transcription of the two reporter proteins. The relative ratio of the reporters can be experimentally measured following mutagenesis of the promoter region allowing for identification of functionally important elements. By systematically altering putative regulatory elements in the promoter, while monitoring expression in both directions, one can very quickly determine useful modifications that can be made to the promoter to provide the amount of regulation, or de-regulation, required for specific applications. (3) Normally position effects must be considered when different expression levels are measured in individual transformants (Menne et al 1994). These assays are expected to be independent of number of copies integrated into a genome or the number of non-integrative and self-replicating copies in a cell.

To simultaneously assess the relative expression levels in both directions from this bi-directional promoter, oligonucleotide primers were designed to re-engineer the maltase/maltose permease promoter such that fluorescent reporter genes could be inserted on both ends. Two color variants of the *Aequorea Victoria* green fluorescent protein (EGFP) were selected as the reporters as they allow for simultaneous examination of regulation of both orientations of the promoter. The cyan colour variant (ECFP) has an excitation major peak at 433 nm and a minor peak at 453 nm. The yellow colour variant (EYFP) has an excitation peak at 513 nm. ECFP has a major emission peak at 475 nm and a minor emission peak at 501 nm. EYFP, however, has a major emission peak at 527 nm. The differences in excitation and emission spectra of ECFP and EYFP allows for simultaneous expression of both reporters and subsequent analysis of the cells or culture media using appropriate filter sets to isolate fluorescence from either chromophore.

Cloning sites for in-frame insertion of the fluorescent reporter genes were added to the maltase/maltose permease promoter by tailed PCR. The Forward primer contained AjlII, NheI, BamHI sites for the directional cloning of the EYFP (yellow fluorescent protein) coding sequence into the NheI/AflII region of the left hand linker [SEQ ID NO: 11]. The return primer contained BamHI, Bgl II and NotI sites for the directional cloning of the ECFP (cyan fluorescent protein) coding region into the BglII/NotI region of the right hand linker linker [SEQ ID NO: 12].

Figure 8:
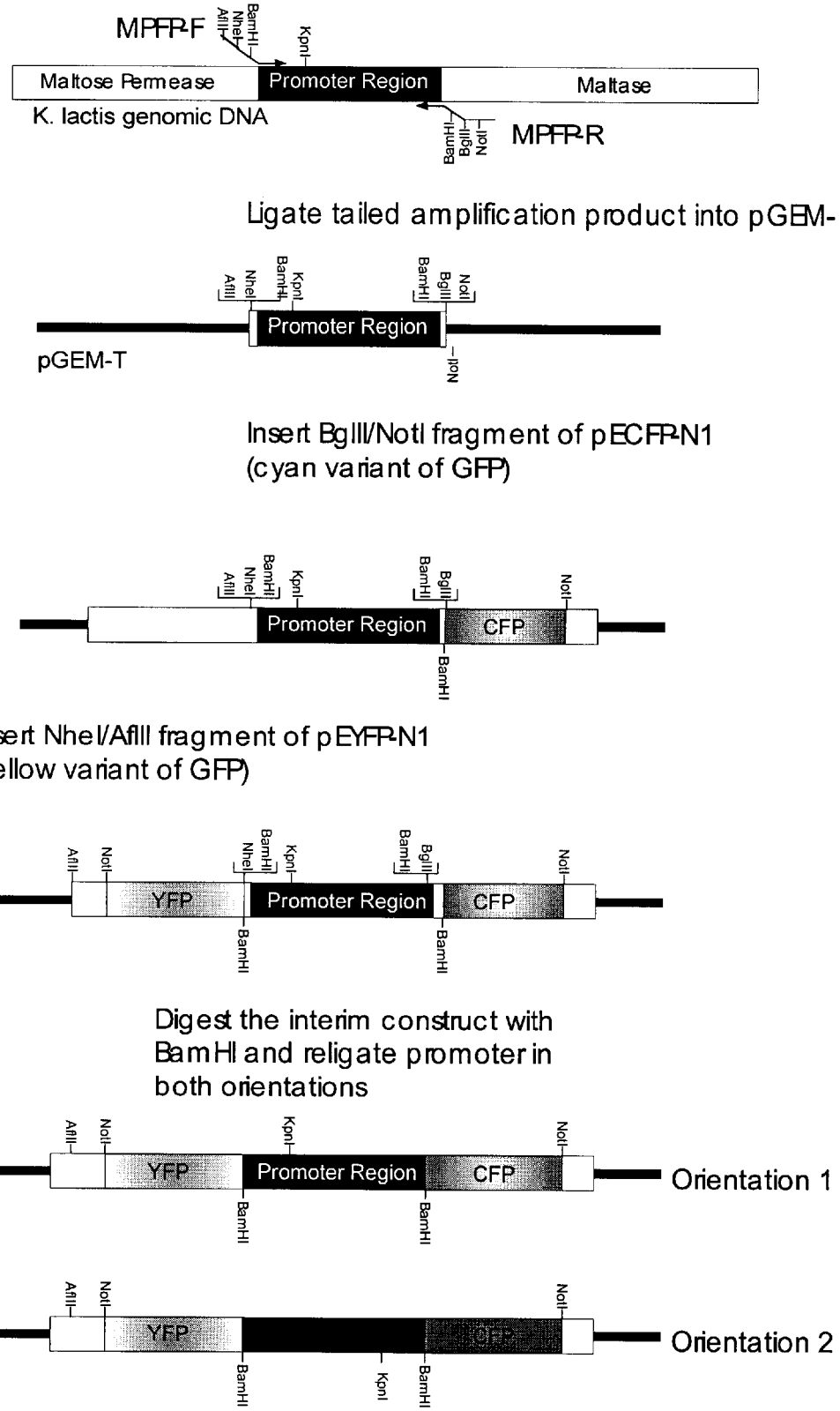

The promoter region was amplified from *K. lactis* (CBS 1065) genomic DNA using high fidelity AmpiTaq polymerase and cloned into the multiple cloning site of the pGEM-T vector. The pGEM-T vector contained a NotI site in the multiple cloning site and the orientation of the amplified DNA was checked via restriction analysis to ensure that the NotI site of the inserted DNA was immediate adjacent to the natural NotI site of the pGEM-T vector (FIG. 8). To add the first reporter to the construct the coding region of the CFP reporter gene was digested from the plasmid vector pECFP-N1with BglII and NotI and directionally cloned into the cassette. Following sequence verification of the interim vector the second marker gene (EYFP) was inserted into the construct by the replacement of the short NheI/AflII fragment of the MCS by the directional cloning of the NheI/AflII fragment from pEYFP-N1. To bring both the ECFP and EYFP coding regions into the correct reading frames with the maltase and maltose permease promoters respectively, the construct was digested with BamHI and the promoter region religated back into the vector. This was done to remove the short BamHI fragments containing the NheI and BglII sites that were necessary for the initial construction but were no longer required (FIG. 8).

Flexibility was built into the expression cassette such that the orientation of the promoter with regard to the reporters could be inverted. In the first orientation the EFCP is transcribed in the maltase direction and the EYFP in the permease direction. The entire promoter region can be removed via the paired BamHI sites and the orientation reversed with respect to the reporter genes by reinsertion of the BamHI fragment and selection of clones having an inverted promoter. The orientation of individual clones can be checked by restriction digestion with the constant site AJM and an asymmetric site within the promoter such as KpnI. In the opposite orientation the EYFP will be transcribed in the maltase direction and ECFP in the permease direction (FIG. 8). The relative expression levels of both the ECFP and EYFP can thus be assessed for both orientations of the promoter. There is an internal control built into each experiment as the relative level of expression, rather than the absolute level of expression, is measured. This is important as the absolute level of expression can depend on the number and position of the integration cassettes.

A further advantage to this expression cassette is that it permits site-specific alterations to be made to the maltase/maltose permease promoter which can then be swapped back into the expression cassette via the paired BamHI sites at either end of the promoter. This permits the functional analysis of the promoter region as changes to the primary promoter sequence could affect transcription in the maltase direction, the permease direction, or both. Important binding sites for regulatory proteins can thereby be mapped onto the promoter region. The effects of specific changes to binding domains, such as the Mig1p, Lac9p, and the UAS can therefore be assessed and related to the availability of specific carbon sources and nutritional regime during the fermentation process.

The relative expression levels of the ECFP and EYPF can also be used to deduce the expression of a heterologous protein inserted in either direction. For example: If there is a 3:1 expression of ECFP:EYFP and the ECFP is swapped for another unknown protein then transformants which produce high levels of the unknown protein can be screened using the EYGP expression. Since it is anticipated that the unknown protein will be expressed in a 3:1 ratio to EYFP it would therefore be possible to use the expression of an easily assayed reporter in one direction as a measure of the rate of expression of any other gene in the opposite direction. This could be a very useful tool for quantifying in vivo expression of a protein which is normally difficult to assay. With the appropriate reporter, such as is provided by fluorescent marker proteins, it would also be possible to automate the screening of high-production transformants.

This bi-directional expression system also has potential use beyond the study of regulatory elements. If the maltase promoter is found to require a transcription factor to enhance expression, the gene coding that protein factor can be placed on the same expression cassette as the gene of interest thus ensuring that expression is not rate-limited by availability of the enhancing factor. For example: A K. lactis homologue of the S. cereviseae positive activator MAL63 could be placed under the regulation of the maltose permease promoter. The positive activator would create a feedback loop enhancing its own expression in addition to enhancing the expression of any reporter or heterologous product being driven by the maltase promoter. The positive activator would not be rate limiting no matter how many copies of the expression cassette are present in the transformed cell.

Finally, if the same protein is driven in both directions from the maltase/maltose permease promoter then there is a more efficient expression for every copy integrated into the genome or for every copy of the construct resident as a self-replicating piece of DNA. This would enhance the production of heterologous product.

We claim:

1. An isolated DNA sequence selected from the group consisting of:
   (a) SEQ ID NO:1;
   (b) the reverse complement of SEQ ID NO:1; and
   (c) a fragment of (a),
   wherein said DNA sequence possesses transcriptional promoter activity in either direction.

2. A recombinantly prepared DNA comprising SEQ ID No: 1.

3. A recombinantly prepared DNA according to claim 2, further comprising one or more structural genes.

4. The DNA of claim 3 further comprising signals permitting the sub-cellular targeting, surface localization or secretion of an expression product of said structural genes.

5. The DNA of claim 3 wherein said DNA comprises a bidirectional promoter and said genes are inserted on each side of the promoter in opposite orientations.

6. An autonomously replicating or integrative expression plasmid comprising the DNA of claim 3.

7. A transformed cell containing a DNA sequence according to claim 1.

8. A transformed cell according to claim 8, wherein said cell is a filamentous fungus.

9. A transformed cell according to claim 8, wherein said cell is a filamentous fungus of the Ophiostoma genus.

10. A transformed cell according to claim 7, wherein said cell it is a yeast cell.

11. A transformed cell according to claim 10, wherein said cell is a yeast cell of the Kluyveromyces genus.

12. A process for the preparation of a recombinant by expression of a gene encoding said protein in a cellular host comprising providing a cell comprising said gene under the transcription control of a sequence according to claim 1, culturing said cell under conditions permitting the gene to express said protein and collecting said recombinant protein.

13. The process according to claim 12 wherein said protein is Endopolygalacturonase from the genus Ophiostoma.

14. The process of claim 12, comprising simultaneous expression of two genes, wherein one of said genes is inserted on one side of the promoter in the sequence and the other of said genes is inserted on the other side whereby said genes are transcribed in opposite directions.

15. The process of claim 14 whereby the expression level of the gene in one direction is predictive of the expression level of the gene in the opposite direction.

16. The process of claim 14 whereby one of the genes is a positive activator which causes enhanced transcription from the promoter in the opposite direction.

* * * * *

UNITED STATES PATENT AND TRADEMARK OFFICE
CERTIFICATE OF CORRECTION

PATENT NO.    : 6,596,513 B2
DATED         : July 24, 2001
INVENTOR(S)   : Williams et al.

It is certified that error appears in the above-identified patent and that said Letters Patent is hereby corrected as shown below:

<u>Title page,</u>
Item [56], References Cited, PUBLICATIONS, "vol 144" should be -- vol. 174 --.

<u>Column 3,</u>
Line 12, "a-aminoadipyl" should be -- α-aminodipyl --.

<u>Column 6,</u>
Line 60, "*labicans*" should be -- *albicans* --.

<u>Column 7,</u>
Line 6, "pennease" should be -- permease --.
Line 25, "*labicans*" should be -- *albicans* --.

<u>Column 8,</u>
Line 30, "*labicans*" should be -- *albicans* --.

<u>Column 9,</u>
Line 31, "–551" should be -- –511 --.

<u>Column 10,</u>
Line 16, "KILAC4" should be -- K1LAC4 --.
Lines 17 and 25, "KILAC12" should be -- K1LAC12 --.

<u>Column 11,</u>
Lines 31-32, the paragraph beginning "DNA of K. lactis" on line 32 should not begin a new paragraph, but should continue the sentence on line 31.
Line 63, "[SEQ ID) NO: 10]" should be -- [SEQ ID NO: 10] --.
Line 64, "N-terninal" should be -- N-terminal --.

<u>Column 14,</u>
Line 4, "AjlII" should be -- *Afl*II --.
Line 21, "pECFP-N1with" should be -- pECFP-N1 with --.
Line 44, "AJM" should be -- *Afl*II --.

UNITED STATES PATENT AND TRADEMARK OFFICE
CERTIFICATE OF CORRECTION

PATENT NO. : 6,596,513 B2
DATED : July 24, 2001
INVENTOR(S) : Williams et al.

It is certified that error appears in the above-identified patent and that said Letters Patent is hereby corrected as shown below:

Column 35,
Line 33, "according to claim 8" should be -- according to claim 7 --.

Column 36,
Line 15, "a recombinant by" should be -- a recombinant protein by --.

Signed and Sealed this

Twenty-seventh Day of January, 2004

JON W. DUDAS
*Acting Director of the United States Patent and Trademark Office*

SEQUENCE LISTING

<160> NUMBER OF SEQ ID NOS: 24

<210> SEQ ID NO 1
<211> LENGTH: 1069
<212> TYPE: DNA
<213> ORGANISM: Kluyveromyces lactis
<220> FEATURE:
<221> NAME/KEY: promoter
<222> LOCATION: (1)..(1069)
<223> OTHER INFORMATION: Maltase promoter sequence

<400> SEQUENCE: 1

```
ttgccacgct agaactatgt tgtcgatcaa cccacgccag ttaatgtcat atttataaga         60
attatcacag ctttcctcat actggatatt gtcatgaagc tcaagaacat tgtttgtact        120
gacatctaga ataatgaggt gaagtgatta aatcggggac cagaacacag aaaaaccctg        180
cacagccgtt tttacttttt tcgcactagt tgccgaagaa actgaccgag aattgtactc        240
cattgaaatc cgcatggata cttgactaaa tggtggggta ccagttttgc ttctctctcc        300
gattcaacat ttcataccgt tttaccgcct gaaatggcac ttgcaatgaa tcttttgtga        360
acattctttg ttaccccgga ttttcttccg atgtatgaaa acaaatatgg ggaaaaacat       420
ggtgaagacg gaaaatctct gcatactttt tgtgtttggg aaaccaaagc gacatttgag       480
ataaggctgt tctatagaat tcacgtacag gaaaatttcc acccgtatta cttgtgacca       540
catctgggga gatttcattt tttttgccct tttcactttc ctcacagaaa ctacgttttt       600 cctttccct cgagaaaatt tctccatttt tccgtttccc tcgagcaaag tttctattac        660
ttttagttga aactactaac ttttgttttt caaaaaaaat tggctgcatt caacagaatg       720
gtaataactt cgatagatgg tcatgccaga cgccatctag aacagtacag cacgttgaag       780
aaaggtgtgg ggaaaacgct gtttctagtt ccaccccaaa aactcatgac tccacccggt       840
ctctttcaag gtgtatcttg tctagcataa catcaaacag atagtcatat tactgtcatg       900
tctgttcagc tggataaaac ttgctcaatt gttaagtgtt acaaaccagg accagaaaga       960
ttataaaaaa gcgttattcc aaaggtatga caggacgatc gctgcaagaa aaaataagag      1020
agaatagact caaacagatc gaaacgttaa gcgcaaaaaa acatcaagt                  1069
```

<210> SEQ ID NO 2

```
<211> LENGTH: 1069
<212> TYPE: DNA
<213> ORGANISM: Kluyveromyces lactis
<220> FEATURE:
<221> NAME/KEY: promoter
<222> LOCATION: (1)..(1069)
<223> OTHER INFORMATION: Maltose permease promoter

<400> SEQUENCE: 2
acttgatgtt tttttgcgct taacgtttcg atctgtttga gtctattctc tcttattttt      60
tcttgcagcg atcgtcctgt catacctttg gaataacgct tttttataat ctttctggtc     120
ctggtttgta acacttaaca attgagcaag ttttatccag ctgaacagac atgacagtaa     180
tatgactatc tgtttgatgt tatgctagac aagatacacc ttgaaagaga ccgggtggag     240
tcatgagttt ttggggtgga actagaaaca gcgttttccc cacacctttc ttcaacgtgc     300
tgtactgttc tagatggcgt ctggcatgac catctatcga agttattacc attctgttga     360
atgcagccaa tttttttttga aaacaaaag ttagtagttt caactaaaag taatagaaac     420
tttgctcgag ggaaacggaa aaatggagaa attttctcga gggaaaagga aaacgtagt     480 ttctgtgagg aaagtgaaaa gggcaaaaaa aatgaaatct ccccagatgt ggtcacaagt     540
aatacgggtg gaaattttcc tgtacgtgaa ttctatagaa cagccttatc tcaaatgtcg     600
ctttggtttc ccaaacacaa aaagtatgca gagattttcc gtcttcacca tgttttcc     660 catatttgtt ttcatacatc ggaagaaaat ccggggtaac aaagaatgtt cacaaaagat     720
tcattgcaag tgccatttca ggcggtaaaa cggtatgaaa tgttgaatcg gagagagaag     780
caaaactggt accccaccat ttagtcaagt atccatgcgg atttcaatgg agtacaattc     840
tcggtcagtt tcttcggcaa ctagtgcgaa aaaagtaaaa acggctgtgc aggttttc     900 tgtgttctgg tccccgattt aatcacttca cctcattatt ctagatgtca gtacaaacaa     960
tgttcttgag cttcatgaca atatccagta tgaggaaagc tgtgataatt cttataaata    1020
tgacattaac tggcgtgggt tgatcgacaa catagttcta gcgtggcaa              1069

<210> SEQ ID NO 3
<211> LENGTH: 32
<212> TYPE: DNA
<213> ORGANISM: Artificial Sequence
<220> FEATURE:
<223> OTHER INFORMATION: Degenerate primer for amplification of maltase
      gene fragment
<220> FEATURE:
<221> NAME/KEY: misc_feature
<222> LOCATION: (3)..(18)
<223> OTHER INFORMATION: n represents a, c, t/u, or g and y represents
      t/u or c

<400> SEQUENCE: 3
cayccncaga cngayccnaa gtggtggaag cc                                    32

<210> SEQ ID NO 4
<211> LENGTH: 33
<212> TYPE: DNA
<213> ORGANISM: Artificial Sequence
<220> FEATURE:
<223> OTHER INFORMATION: Degenerate primer for amplification of maltase
      gene fragment
<220> FEATURE:
<221> NAME/KEY: Unsure
<222> LOCATION: (6)..(6)
<223> OTHER INFORMATION:
<220> FEATURE:
<221> NAME/KEY: Unsure
<222> LOCATION: (12)..(12)
```

```
<223> OTHER INFORMATION:
<220> FEATURE:
<221> NAME/KEY: Unsure
<222> LOCATION: (18)..(18)
<223> OTHER INFORMATION:
<220> FEATURE:
<221> NAME/KEY: misc_feature
<222> LOCATION: (1)..(28)
<223> OTHER INFORMATION: n represents a, c, t/u, or g;  y represents
      t/u or c; r represents g or a

<400> SEQUENCE: 4
rcartcytcg ttctcccagt tnagrtcngg ctg                                33

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide primer for the inverse PCR of
      the MAL locus
<220> FEATURE:
<221> NAME/KEY: Unsure
<222> LOCATION: (22)..(22)
<223> OTHER INFORMATION:

<400> SEQUENCE: 5
caatggcaaa ccaattcctc ccaat                                         25

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide primer for the inverse PCR of
      the MAL locus

<400> SEQUENCE: 6
cagatccaaa tcgcgttagc tccaa                                         25

<210> SEQ ID NO 7
<211> LENGTH: 52
<212> TYPE: DNA
<213> ORGANISM: Artificial Sequence
<220> FEATURE:
<223> OTHER INFORMATION: Oligonucleotide primer for the construction of
      the basic expression cassette

<400> SEQUENCE: 7
ggggcccaag cttgggggggg gatccttgcc acgctagaac tatgttgtcg at          52

<210> SEQ ID NO 8
<211> LENGTH: 70
<212> TYPE: DNA
<213> ORGANISM: Artificial Sequence
<220> FEATURE:
<223> OTHER INFORMATION: Oligonucleotide primer for the construction of
      the basic expression cassette

<400> SEQUENCE: 8
ggggcccggt accgacgacg ctagcttaat taagggccgg catgcttgta gttttttgcg   60
cttaacgtcg                                                          70

<210> SEQ ID NO 9
<211> LENGTH: 48
<212> TYPE: DNA
<213> ORGANISM: Artificial Sequence
<220> FEATURE:
```

<223> OTHER INFORMATION: Oligonucleotide primer for the reengineering of
      the endopolygalacturonase gene

<400> SEQUENCE: 9
ggggtttaag cttgtcgacg catgctgggc atcactactc tgctagtg         48

<210> SEQ ID NO 10
<211> LENGTH: 45
<212> TYPE: DNA
<213> ORGANISM: Artificial Sequence
<220> FEATURE:
<223> OTHER INFORMATION: Oligonucleotide primer for the reengineering of
      the endopolygalacturonase gene

<400> SEQUENCE: 10
ggggtttgaa ttcaattaat tcttgatctg cagcaggggt cccgc            45

<210> SEQ ID NO 11
<211> LENGTH: 51
<212> TYPE: DNA
<213> ORGANISM: Artificial Sequence
<220> FEATURE:
<223> OTHER INFORMATION: Oligonucleotide primer for the construction of
      the bi-directional fluorescent marker cassette

<400> SEQUENCE: 11
gggtttcctt aaggctagcg gatccttgcc acgctagaac tatgttgtcg a     51

<210> SEQ ID NO 12
<211> LENGTH: 55
<212> TYPE: DNA
<213> ORGANISM: Artificial Sequence
<220> FEATURE:
<223> OTHER INFORMATION: Oligonucleotide primer for the construction of
      the bi-directional fluorescent marker cassette

<400> SEQUENCE: 12
gggttttgcg gccgcagatc tggatccact tgatgttttt ttgcgcttaa cgttt  55

<210> SEQ ID NO 13
<211> LENGTH: 50
<212> TYPE: PRT
<213> ORGANISM: kluyveromyces lactis

<400> SEQUENCE: 13

Thr Ile Thr Lys Glu Ser Glu Pro Gln Thr Asp Asp Lys Trp Trp Lys
1               5                   10                  15

Glu Ala Gln Pro Asp Leu Asn Trp Gly Asn Glu Asp Leu Asn Ala Ile
            20                  25                  30

Tyr Glu Ser Ala Val Gly Phe Trp Leu Asp His Gly Val Asp Gly Phe
        35                  40                  45

Arg Ile
    50

<210> SEQ ID NO 14
<211> LENGTH: 584
<212> TYPE: PRT
<213> ORGANISM: Saccharomyces carlsbergensis

<400> SEQUENCE: 14

Met Thr Ile Ser Asp His Pro Glu Thr Glu Pro Lys Trp Trp Lys Glu
1               5                   10                  15

Ala Thr Ile Tyr Gln Ile Tyr Pro Ala Ser Phe Lys Asp Ser Asn Asn
            20                  25                  30

-continued

```
Asp Gly Trp Gly Asp Leu Lys Gly Ile Thr Ser Lys Leu Gln Tyr Ile
            35                  40                  45
Lys Asp Leu Gly Val Asp Ala Ile Trp Val Cys Pro Phe Tyr Asp Ser
         50                  55                  60
Pro Gln Gln Asp Met Gly Tyr Asp Ile Ser Asn Tyr Glu Lys Val Trp
 65                  70                  75                  80
Pro Thr Tyr Gly Thr Asn Glu Asp Cys Phe Glu Leu Ile Asp Lys Thr
                 85                  90                  95
His Lys Leu Gly Met Lys Phe Ile Thr Asp Leu Val Ile Asn His Cys
            100                 105                 110
Ser Thr Glu His Glu Trp Phe Lys Glu Ser Arg Ser Ser Lys Thr Asn
         115                 120                 125
Pro Lys Arg Asp Trp Phe Phe Trp Arg Pro Pro Lys Gly Tyr Asp Ala
130                 135                 140
Glu Gly Lys Pro Ile Pro Pro Asn Asn Trp Lys Ser Phe Phe Gly Gly
145                 150                 155                 160
Ser Ala Trp Thr Phe Asp Glu Thr Thr Asn Glu Phe Tyr Leu Arg Leu
                165                 170                 175
Phe Ala Ser Arg Gln Val Asp Leu Asn Trp Glu Asn Glu Asp Cys Arg
            180                 185                 190
Arg Ala Ile Phe Glu Ser Ala Val Gly Phe Trp Leu Asp His Gly Val
         195                 200                 205
Asp Gly Phe Arg Ile Asp Thr Ala Gly Leu Tyr Ser Lys Arg Pro Gly
210                 215                 220
Leu Pro Asp Ser Pro Ile Phe Asp Lys Thr Ser Lys Leu Gln His Pro
225                 230                 235                 240
Asn Trp Gly Ser His Asn Gly Pro Arg Ile His Glu Tyr His Gln Glu
                245                 250                 255
Leu His Arg Phe Met Lys Asn Arg Val Lys Asp Gly Arg Glu Ile Met
            260                 265                 270
Arg Val Gly Glu Val Ala His Gly Ser Asp Asn Ala Leu Tyr Thr Ser
         275                 280                 285
Ala Ala Arg Tyr Glu Val Ser Glu Val Phe Ser Phe Thr His Val Glu
290                 295                 300
Val Gly Thr Ser Pro Phe Phe Arg Tyr Asn Ile Val Pro Phe Thr Leu
305                 310                 315                 320
Lys Gln Trp Lys Glu Ala Ile Ala Ser Asn Phe Leu Phe Ile Asn Gly
                325                 330                 335
Thr Asp Ser Trp Ala Thr Thr Tyr Ile Glu Asn His Asp Gln Ala Arg
            340                 345                 350
Ser Ile Thr Arg Phe Ala Asp Asp Ser Pro Lys Tyr Arg Lys Ile Ser
         355                 360                 365
Gly Lys Leu Leu Thr Leu Leu Glu Cys Ser Leu Thr Gly Thr Leu Tyr
370                 375                 380
Val Tyr Gln Gly Gln Glu Ile Gly Gln Ile Asn Phe Lys Glu Trp Pro
385                 390                 395                 400
Ile Glu Lys Tyr Glu Asp Val Asp Val Lys Asn Asn Tyr Glu Ile Ile
                405                 410                 415
Lys Lys Ser Phe Gly Lys Asn Ser Lys Glu Met Lys Asp Phe Phe Lys
            420                 425                 430
Gly Ile Ala Leu Leu Ser Arg Asp His Ser Arg Thr Pro Met Pro Trp
         435                 440                 445
```

-continued

```
Thr Lys Asp Lys Pro Asn Ala Gly Phe Thr Gly Pro Asp Val Lys Pro
    450                 455                 460

Trp Phe Phe Leu Asn Glu Ser Phe Glu Gln Gly Ile Asn Val Glu Gln
465                 470                 475                 480

Glu Ser Arg Asp Asp Ser Val Leu Asn Phe Trp Lys Arg Ala Leu
                485                 490                 495

Gln Ala Arg Lys Lys Tyr Lys Glu Leu Met Ile Tyr Gly Tyr Asp Phe
            500                 505                 510

Gln Phe Ile Asp Leu Asp Ser Asp Gln Ile Phe Ser Phe Thr Lys Glu
            515                 520                 525

Tyr Glu Asp Lys Thr Leu Phe Ala Ala Leu Asn Phe Ser Gly Glu Glu
        530                 535                 540

Ile Glu Phe Ser Leu Pro Arg Glu Gly Ala Ser Leu Ser Phe Ile Leu
545                 550                 555                 560

Gly Asn Tyr Asp Asp Thr Asp Val Ser Ser Arg Val Leu Lys Pro Trp
                565                 570                 575

Glu Gly Arg Ile Tyr Leu Val Lys
            580
```

<210> SEQ ID NO 15
<211> LENGTH: 589
<212> TYPE: PRT
<213> ORGANISM: Saccharomyces cereviseae

<400> SEQUENCE: 15

```
Met Thr Ile Ser Ser Ala His Pro Glu Thr Glu Pro Lys Trp Trp Lys
1               5                   10                  15

Glu Ala Thr Ile Tyr Gln Ile Tyr Pro Ala Ser Phe Lys Asp Ser Asn
            20                  25                  30

Asn Asp Gly Trp Gly Asp Met Lys Gly Ile Ala Ser Lys Leu Glu Tyr
        35                  40                  45

Ile Lys Glu Leu Gly Ala Asp Ala Ile Trp Ile Ser Pro Phe Tyr Asp
    50                  55                  60

Ser Pro Gln Asp Asp Met Gly Tyr Asp Ile Ala Asn Tyr Glu Lys Val
65                  70                  75                  80

Trp Pro Thr Tyr Gly Thr Asn Glu Asp Cys Phe Ala Leu Ile Glu Lys
                85                  90                  95

Thr His Lys Leu Gly Met Lys Phe Ile Thr Asp Leu Val Ile Asn His
            100                 105                 110

Cys Ser Ser Glu His Glu Trp Phe Lys Glu Ser Arg Ser Ser Lys Thr
        115                 120                 125

Asn Pro Lys Arg Asp Trp Phe Phe Trp Arg Pro Pro Lys Gly Tyr Asp
    130                 135                 140

Ala Glu Gly Lys Pro Ile Pro Pro Asn Asn Trp Arg Ser Tyr Phe Gly
145                 150                 155                 160

Gly Ser Ala Trp Thr Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
        195                 200                 205

Val Asp Gly Phe Arg Ile Asp Val Gly Ser Leu Tyr Ser Lys Val Ala
    210                 215                 220

Gly Leu Pro Asp Ala Pro Val Ile Asp Glu Asn Ser Lys Trp Gln Pro
225                 230                 235                 240
```

```
Ser Asp Pro Phe Thr Met Asn Gly Pro Arg Ile His Glu Phe His Gln
                245                 250                 255

Glu Met Asn Lys Phe Ile Arg Asn Arg Val Lys Asp Gly Arg Glu Ile
            260                 265                 270

Met Thr Val Gly Glu Met Gln His Ala Thr Asp Glu Thr Lys Arg Leu
        275                 280                 285

Tyr Thr Ser Ala Ser Arg His Glu Leu Ser Glu Leu Phe Asn Phe Ser
    290                 295                 300

His Thr Asp Val Gly Thr Ser Pro Lys Phe Arg Gln Asn Leu Ile Pro
305                 310                 315                 320

Tyr Glu Leu Lys Asp Trp Lys Val Ala Leu Ala Glu Leu Phe Arg Tyr
                325                 330                 335

Val Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
        355                 360                 365

Val Ile Ser Gly Lys Leu Leu Ser Val Leu Val Ser Leu Ser Gly
    370                 375                 380

Thr Leu Tyr Val Tyr Gln Gly Gln Glu Leu Gly Glu Ile Asn Phe Lys
385                 390                 395                 400

Asn Trp Pro Ile Glu Lys Tyr Glu Asp Val Glu Val Arg Asn Asn Tyr
                405                 410                 415

Asp Ala Ile Lys Glu Glu His Gly Glu Asn Ser Lys Glu Met Lys Arg
            420                 425                 430

Phe Leu Glu Ala Ile Ala Leu Ile Ser Arg Asp His Ala Arg Thr Pro
        435                 440                 445

Met Gln Trp Ser Arg Glu Glu Pro Asn Ala Gly Phe Ser Gly Pro Asn
    450                 455                 460

Ala Lys Pro Trp Phe Tyr Leu Asn Glu Ser Phe Arg Glu Gly Ile Asn
465                 470                 475                 480

Ala Glu Asp Glu Ser Lys Asp Pro Asn Ser Val Leu Asn Phe Trp Lys
                485                 490                 495

Glu Ala Leu Arg Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
        515                 520                 525

Thr Lys Lys Tyr Asp Asn Lys Thr Leu Phe Ala Ala Leu Asn Phe Ser
    530                 535                 540

Ser Asp Ser Ile Asp Phe Thr Ile Pro Asn Asn Ser Ser Phe Lys
545                 550                 555                 560

Leu Glu Phe Gly Asn Tyr Pro Arg Ser Glu Val Asp Ala Ser Ser Arg
                565                 570                 575

Thr Leu Lys Pro Trp Glu Gly Arg Ile Tyr Ile Ser Glu
            580                 585

<210> SEQ ID NO 16
<211> LENGTH: 568
<212> TYPE: PRT
<213> ORGANISM: Candida albicans

<400> SEQUENCE: 16

Met Ser Glu His Lys Trp Trp Lys Glu Ala Val Val Tyr Gln Ile Trp
1               5                   10                  15

Pro Ala Ser Tyr Lys Asp Ser Asn Gly Asp Gly Val Gly Asp Ile Pro
```

```
                 20                  25                  30
Gly Ile Ile Ser Thr Leu Asp Tyr Ile Ala Ser Leu Gly Val Thr Thr
             35                  40                  45
Val Trp Leu Ser Pro Met Tyr Asp Ser Pro Gln Asp Met Gly Tyr
 50                  55                  60
Asp Val Ser Asp Tyr Glu Asn Val Tyr Ser Lys Tyr Gly Thr Leu Gln
 65                  70                  75                  80
Asp Met Asp Arg Leu Ile Ala Gly Cys His Asp Arg Gly Leu Lys Leu
             85                  90                  95
Ile Leu Asp Leu Val Ile Asn His Thr Ser Val Glu His Lys Trp Phe
             100                 105                 110
Lys Glu Ser Arg Leu Ser Lys Asp Asn Pro Lys Arg Asp Trp Tyr Ile
             115                 120                 125
Trp Lys Pro Pro Arg Ile Asp Ser Asn Gly Asn Lys His Pro Pro Asn
 130                 135                 140
Asn Trp Gly Ser Tyr Phe Ser Gly Ser Ala Trp Lys Tyr Asp Glu Leu
 145                 150                 155                 160
Thr Gly Glu Tyr Tyr Leu His Leu Phe Ala Glu Ser Gln Pro Asp Leu
             165                 170                 175
Asn Trp Glu Asn Lys Glu Cys Arg Glu Ala Ile Tyr Asn Ser Ala Ile
             180                 185                 190
Lys Phe Trp Leu Asp Lys Gly Val Asp Gly Phe Arg Ile Asp Thr Ala
             195                 200                 205
Gly Met Tyr Ser Lys Tyr Gln His Phe Lys Asp Ala Pro Val Ala Phe
             210                 215                 220
Pro Asp Thr Glu Phe Gln Cys Glu Ile Tyr His Lys Asn Gly Pro Arg
 225                 230                 235                 240
Ile His Glu Phe His Lys Glu Met Ala Lys Val Met Glu Pro Tyr Asp
             245                 250                 255
Thr Met Thr Val Gly Glu Val Gly His Ser Thr Arg Glu Gln Ala Leu
             260                 265                 270
Lys Tyr Val Ser Ala Ala Glu Lys Glu Met Asn Met Phe Leu Phe
             275                 280                 285
Asp Val Val Glu Leu Gly Ser Asp Pro Arg Asp Arg Phe Arg Tyr Asn
 290                 295                 300
Gly Phe Asp Leu Val Asp Leu Lys Lys Ala Ile Lys Ser Gln Gly Glu
 305                 310                 315                 320
Phe Ala Glu Gly Thr Asp Ala Trp Ser Thr Val Phe Ile Glu Asn His
             325                 330                 335
Asp Gln Ala Arg Ala Ile Ser Arg Phe Gly Asn Asp Ser Pro Glu Phe
             340                 345                 350
Arg Val Leu Ser Gly Lys Ala Ile Ala Met Leu Gln Cys Cys Leu Thr
             355                 360                 365
Gly Thr Leu Phe Ile Tyr Gln Gly Gln Glu Ile Gly Met Thr Asn Val
             370                 375                 380
Pro Arg Ser Trp Pro Ile Glu Glu Tyr Lys Asp Ile Asn Thr Ile Asn
 385                 390                 395                 400
Tyr Tyr Arg Ala Phe Lys Glu Lys Tyr Gly Lys Asp Ala Asp Tyr Lys
             405                 410                 415
Gln Lys Glu Glu Lys Leu Val Asp Val Ile Asn Arg Leu Ala Arg Asp
             420                 425                 430
Asn Ala Arg Thr Pro Val Gln Trp Ser His Gln Gln Tyr Ala Gly Phe
             435                 440                 445
```

```
Ser Glu Val Glu Pro Trp Met Arg Val Asn Asp Asn Tyr Lys Glu Ile
    450                 455                 460

Asn Val Glu Asp Gln Asp Gly Asp Asp His Ser Leu Leu Asn Phe Tyr
465                 470                 475                 480

Arg Lys Leu Leu Lys Leu Arg Gly Glu Tyr Lys Asp Leu Phe Val Tyr
                485                 490                 495

Gly Glu Met Lys Phe Leu Asp Phe Asp Asp Lys Lys Leu Phe Thr Phe
                500                 505                 510

Ala Lys Gly Ala Pro Gly Ser Pro Val Ala Tyr Ile Val Ile Asn Phe
            515                 520                 525

Ser Gly Glu Asp Val Lys Phe Glu Pro Leu Ile Lys Gly Asn Tyr Lys
    530                 535                 540

Leu Val Leu Thr Asn Val Asp Lys Asp Ser Lys Asp Ala Leu Ser Pro
545                 550                 555                 560

Tyr Glu Ala Arg Met Tyr Val Val
                565
```

<210> SEQ ID NO 17
<211> LENGTH: 1109
<212> TYPE: DNA
<213> ORGANISM: Kluyveromyces lactis

<400> SEQUENCE: 17

```
ttgccacgct agaactatgt tgtcgatcaa cccacgccag ttaatgtcat atttataaga      60
attatcacag ctttcctcat actggatatt gtcatgaagc tcaagaacat tgtttgtact     120
gacatctaga ataatgaggt gaagtgatta atcggggac cagaacacag aaaaaccctg     180
cacagccgtt tttatttttt cgcagtagtt gccgaaggaa ctgaccgaga aaaaatccat     240
ttaaatccgg ccttggataa cttggactaa atggtgggt tacccagttt tgcttctctc     300
tcccgattca acatttcata ccgttttacc gccttgaaat ggcacttgca atgaatcttt     360
ttgtgaacat tctttgttac cccgggattt tcttccggat gtatgaaaac aaatatgggg     420
aaaaacatgg tgaagacgga aaatctctgc atacttttg tgtttgggaa accaaagcga     480
catttgagat aaggctgttc tatagaattc acgtacagga aaatttccac ccgtattact     540
tgtgaccaca tctggggaga tttcattttt tttgcccttt tcactttcct cacagaaact     600
acgttttttcc ttttcctcg agaaaatttc tccatttttc cgtttccctc gagcaaagtt     660
tctattactt ttagttgaaa ctactaactt ttgttttca aaaaaaattg gctgcattca     720
acagaatggt aataacttcg atagatggtc atgccagacg ccatctagaa cagtacagca     780
cgttgaagaa aggtgtgggg aaaacgctgt ttctagttcc accccaaaaa ctcatgactc     840
cacccggtct ctttcaaggt gtatcttgtc tagcataaca tcaaacagat agtcatatta     900
ctgtcatgtc tgttcagctg gataaaactt gctcaattgt taagtgttac aaaccaggac     960
cagaaagatt atttaaaaag cgttattcca aggttgacag cgtacgctgc aagaaaaagc    1020
gttattccaa ggttgacagc gtacgctgca agaaaataa gagagaatag accaacgatc    1080
gacgttaagc gcaaaaaact acaagtatg                                     1109
```

<210> SEQ ID NO 18
<211> LENGTH: 20
<212> TYPE: PRT
<213> ORGANISM: Kluyveromyces lactis

<400> SEQUENCE: 18

```
Thr Ile Thr Lys Glu Val Ser Glu His Pro Gln Thr Asp Pro Lys Trp
 1               5                  10                  15

Trp Lys Glu Ala
            20

<210> SEQ ID NO 19
<211> LENGTH: 11
<212> TYPE: PRT
<213> ORGANISM: Artificial Sequence
<220> FEATURE:
<223> OTHER INFORMATION: Degenerate N-terminal sequence

<400> SEQUENCE: 19

His Pro Gln Thr Asp Asp Lys Trp Trp Lys Glu
 1               5                  10

<210> SEQ ID NO 20
<211> LENGTH: 11
<212> TYPE: PRT
<213> ORGANISM: Artificial Sequence
<220> FEATURE:
<223> OTHER INFORMATION: Conserved region of maltase peptide

<400> SEQUENCE: 20

Gln Asp Asp Leu Asn Trp Glu Asn Glu Asp Leu
 1               5                  10

<210> SEQ ID NO 21
<211> LENGTH: 11
<212> TYPE: DNA
<213> ORGANISM: Saccharomyces cereviseae
<220> FEATURE:
<221> NAME/KEY: misc_feature
<222> LOCATION: (5)..(5)
<223> OTHER INFORMATION: w represents a or t/u

<400> SEQUENCE: 21
gaaawtttcg c                                                        11

<210> SEQ ID NO 22
<211> LENGTH: 11
<212> TYPE: DNA
<213> ORGANISM: Kluyveromyces lactis

<400> SEQUENCE: 22
gaaattttcc t                                                        11

<210> SEQ ID NO 23
<211> LENGTH: 11
<212> TYPE: DNA
<213> ORGANISM: Kluyveromyces lactis

<400> SEQUENCE: 23
gaaattttct c                                                        11

<210> SEQ ID NO 24
<211> LENGTH: 17
<212> TYPE: DNA
<213> ORGANISM: Saccharomyces cereviseae
<220> FEATURE:
<221> NAME/KEY: misc_feature
```

```
<222> LOCATION: (5)..(13)
<223> OTHER INFORMATION: s represents g or c

<400> SEQUENCE: 24
cggasgacag tcstccg                                                17
```